United States Patent
Imaeda

(10) Patent No.: US 10,196,974 B2
(45) Date of Patent: Feb. 5, 2019

(54) HEAT GENERATION RATE WAVEFORM CALCULATION DEVICE OF INTERNAL COMBUSTION ENGINE AND METHOD FOR CALCULATING HEAT GENERATION RATE WAVEFORM

(71) Applicant: TOYOTA JIDOSHA KABUSHIKI KAISHA, Toyota-shi, Aichi (JP)

(72) Inventor: Munenori Imaeda, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 324 days.

(21) Appl. No.: 15/305,033

(22) PCT Filed: Feb. 9, 2015

(86) PCT No.: PCT/JP2015/053494
§ 371 (c)(1),
(2) Date: Oct. 18, 2016

(87) PCT Pub. No.: WO2015/162970
PCT Pub. Date: Oct. 29, 2015

(65) Prior Publication Data
US 2017/0184019 A1 Jun. 29, 2017

(30) Foreign Application Priority Data

Apr. 22, 2014 (JP) .................. 2014-088034

(51) Int. Cl.
*F02D 35/02* (2006.01)
*F02B 77/08* (2006.01)
(Continued)

(52) U.S. Cl.
CPC ............ *F02B 77/084* (2013.01); *F02D 35/02* (2013.01); *F02D 35/028* (2013.01); *F02D 37/02* (2013.01);
(Continued)

(58) Field of Classification Search
CPC ........ F02D 35/02; F02D 35/028; F02D 37/02; F02D 41/009; F02D 2041/1433;
(Continued)

(56) References Cited

U.S. PATENT DOCUMENTS

| 8,831,856 B2 | 9/2014 | Yasuda et al. |
| 9,885,295 B2 * | 2/2018 | Imaeda ................... F02D 45/00 |

FOREIGN PATENT DOCUMENTS

| EP | 2415996 A1 | 2/2012 |
| EP | 2860380 A1 | 4/2015 |

(Continued)

*Primary Examiner* — Hieu T Vo
(74) *Attorney, Agent, or Firm* — Oliff PLC

(57) ABSTRACT

A first-half combustion period, for example, is estimated/evaluated, with a required accuracy, more simply than the conventional art, while reducing man-hours to produce a heat generation rate waveform of an internal combustion engine. Within a combustion period of an air-fuel mixture, a period from an ignition time FA to a heat generation rate maximum time dQpeakA where the heat generation rate is maximum is defined as the first-half combustion period a that is one of characteristic values of the heat generation rate waveform. The first-half combustion period a is estimated based on an in-cylinder volume at the heat generation rate maximum time, and furthermore by being corrected using an exponential function of the engine rotation speed with a value depending on a tumble ratio as exponent. Thus, the heat generation rate waveform is produced using the estimated first-half combustion period a.

17 Claims, 12 Drawing Sheets

(51) Int. Cl.
  *F02D 41/00* (2006.01)
  *F02D 37/02* (2006.01)
  *G01N 25/22* (2006.01)
  *G01N 31/12* (2006.01)
  *F02D 41/14* (2006.01)

(52) U.S. Cl.
  CPC ........... *F02D 41/009* (2013.01); *G01N 25/22* (2013.01); *G01N 31/12* (2013.01); *F02D 2041/1433* (2013.01); *F02D 2200/101* (2013.01)

(58) Field of Classification Search
  CPC . F02D 2200/101; F02B 77/084; G01N 25/22; G01N 31/12
  See application file for complete search history.

(56) References Cited

FOREIGN PATENT DOCUMENTS

| | | |
|---|---|---|
| JP | 2007-177654 A | 7/2007 |
| JP | 2007-255237 A | 10/2007 |
| JP | 2011-106334 A | 6/2011 |
| JP | 4893857 B2 | 3/2012 |
| JP | 5257520 B2 | 8/2013 |
| JP | 2014-025380 A | 2/2014 |
| JP | 5716869 B2 | 5/2015 |
| WO | 2011/036794 A1 | 3/2011 |
| WO | 2011/132253 A1 | 10/2011 |
| WO | 2013/183163 A1 | 12/2013 |

\* cited by examiner

ρ fuel@SA (a)

(b)

HEAT GENERATION RATE WAVEFORM CALCULATION DEVICE OF INTERNAL COMBUSTION ENGINE AND METHOD FOR CALCULATING HEAT GENERATION RATE WAVEFORM

TECHNICAL FIELD

The present invention relates to a device for calculating a heat generation rate waveform of a spark-ignition internal combustion engine and a method therefor, and in particular, to technique for obtaining a heat generation rate waveform by focusing attention on a period from ignition of an air-fuel mixture to a time where the heat generation rate is maximum (in this Specification, the above period is referred to as "first-half combustion period").

BACKGROUND ART

Conventionally, the heat generation rate in a cylinder is approximated by the Wiebe function in order to express a combustion state of an internal combustion engine. With the Wiebe function, the heat generation rate waveform can be appropriately expressed by identifying a plurality of parameters. The Wiebe function is used for estimating the heat generation rate or the combustion mass rate due to combustion in the internal combustion engine.

For example, in a method for determining Wiebe function parameters described in Patent Document 1, a shape parameter m of the Wiebe function is identified by a predetermined expression based on a combustion rate at a crank angle where the heat generation rate is maximum. Other parameters such as k, $a/\theta_p^{m+1}$, and $\theta_b$ are also identified by the respective predetermined expressions, thus the Wiebe function can be determined so that it is adapted to an actual heat generation pattern with a high accuracy.

Patent Document 1 describes that, by determining the Wiebe function by identifying the plurality of parameters such as m, k, $a/\theta_p^{m+1}$, and $\theta_b$ under various operation conditions, it is possible to understand the relationships between the above parameters and operation parameters (e.g., the load rate, the rotation speed, the air-fuel ratio and the spark time) of the internal combustion engine. Thus, by using the relationships as understood above, it is possible to determine the Wiebe function under any operation condition of the internal combustion engine, which results in accurate expression of the combustion state of the internal combustion engine.

PRIOR ART DOCUMENT

Patent Document

Patent Document 1: JP 2007-177654A

SUMMARY OF INVENTION

Problem to be Solved by Invention

However, Patent Document 1 does not disclose any specific method for identifying the relationships between the parameters m, k, $a/\theta_p^{m+1}$ and $\theta_b$ of the Wiebe function and the operation parameters of the internal combustion engine. For this reason, the parameters m, k, $a/\theta_p^{m+1}$ and $\theta_b$ should be actually identified under almost all operation conditions so as to determine the Wiebe function under the respective operation conditions. That is, in the conventional method, there is still room for further reducing man-hours to produce the heat generation rate waveform and thus reducing costs.

Also, in the above-described method, the entire heat generation rate waveform can be expressed only by identifying the respective parameters m, k, $a/\theta_p^{m+1}$ and $\theta_b$ to determine the Wiebe function, and based on the above, it is possible to evaluate the combustion state. Thus, it is not possible to estimate and evaluate, for example, only the first-half combustion period (period from ignition of the air-fuel mixture to the time where the heat generation rate is maximum), without expressing the entire heat generation rate waveform.

The present invention was made in consideration of the above circumstances. An object of the present invention is to reduce man-hours to produce (calculate) the heat generation rate waveform by focusing attention on the first-half combustion period, which is one of the indexes representing the combustion state, so as to estimate and evaluate simply, for example, the first-half combustion period while ensuring a required accuracy.

Means for Solving Problem

—Solution Principles of Invention—

It was newly found, by the Inventor of the present invention, that the first-half combustion period, which is a period from ignition of the air-fuel mixture by spark ignition to the time where the heat generation rate is maximum, is not affected by the engine load rate, the exhaust gas recirculation (EGR) rate, the air-fuel ratio and the oil-water temperature, but highly correlated with the physical quantity at the time where the heat generation rate is maximum.

The solution principles of the present invention are based on such a new finding, which are to use the first-half combustion period as one of characteristic values of the heat generation rate waveform so as to estimate the first-half combustion period based on the physical quantity at the time where the heat generation rate is maximum.

—Solving Means—

Specifically, the present invention is directed to a heat generation rate waveform calculation device that is configured to calculate a heat generation rate waveform of a spark-ignition internal combustion engine. In this device, within a combustion period of an air-fuel mixture, a period from an ignition time to a heat generation rate maximum time where a heat generation rate is maximum is defined as a first-half combustion period that is one of characteristic values of the heat generation rate waveform. Thus, the first-half combustion period is estimated based on a physical quantity at the heat generation rate maximum time, so that the heat generation rate waveform is calculated using the estimated first-half combustion period.

In the above-described configuration, when calculating the waveform of the heat generation rate due to the combustion of the air-fuel mixture in the cylinder of the internal combustion engine, the first-half combustion period, which is a period from the ignition time of the air-fuel mixture to the heat generation rate maximum time where the heat generation rate is maximum, is used as one of the characteristic values of the heat generation rate waveform. It was newly found, by the Inventor of the present invention, that the first-half combustion period is not affected by the operation conditions such as the engine load rate, the EGR rate, the air-fuel ratio and the oil-water temperature, but affected by the physical quantity at the heat generation rate maximum time. Thus, by calculating the heat generation rate waveform based on the first-half combustion period, it is not necessary to consider the above operation conditions. Accordingly, it is possible to reduce man-hours to produce the heat generation rate waveform while ensuring a sufficient accuracy compared with the conventional art in which the heat generation rate waveform is produced in consideration of (specifically, by changing) the operation conditions such as the load rate, the EGR rate, the air-fuel ratio and the oil-water temperature (i.e., the art in which a plurality of parameters such as a shape parameter is identified under the various operation conditions using the Wiebe function).

Also, it is not necessary to produce the entire heat generation rate waveform. As described above, only the first-half combustion period can be estimated based on the physical quantity at the heat generation rate maximum time. Thus, it is possible to simply estimate/evaluate the first-half combustion period while ensuring a required accuracy.

It is considered that the first-half combustion period is highly affected by a turbulence in the cylinder. Specifically, it is considered that when the turbulence in the cylinder increases, the flame propagates more rapidly, which results in decrease in the first-half combustion period. In addition, the turbulence in the cylinder changes according to the in-cylinder volume. That is, as the in-cylinder volume increases at the heat generation rate maximum time (i.e., as the piston is located in the vicinity of the bottom dead center in the combustion stroke), the turbulence in the cylinder reduces. When the turbulence in the cylinder reduces, the flame propagates more slowly, which results in increase in the first-half combustion period. For this reason, when the heat generation rate maximum time is on the delay side of the time where the piston reaches the compression top dead center (TDC), the turbulence in the cylinder reduces as the in-cylinder volume at the heat generation rate maximum time increases, which results in increase in the first-half combustion period. On the other hand, the turbulence in the cylinder increases as the in-cylinder volume at the heat generation rate maximum time decreases, which causes the flame to propagate more rapidly and results in decrease in the first-half combustion period. Like this, the in-cylinder volume at the heat generation rate maximum time is a parameter correlated with the turbulence in the cylinder. Thus, it is preferable to calculate the first-half combustion period based on the in-cylinder volume at the heat generation rate maximum time. In this way, it is possible to calculate the first-half combustion period reflecting the influence of the turbulence in the cylinder, which sufficiently ensures the accuracy in the estimation of the first-half combustion period as well as ensures reliability of the heat generation rate waveform calculated using the first-half combustion period.

Also, the turbulence in the cylinder changes due to the engine rotation speed. That is, as the engine rotation speed decreases, the flow rate of the air that flows from the intake system into the cylinder decreases, which leads to reduction in the turbulence in the cylinder. When the turbulence in the cylinder reduces, the flame propagates more slowly, which results in increase in the first-half combustion period. On the other hand, as the engine rotation speed increases, the flow rate of the air that flows from the intake system into the cylinder increases, which leads to increase in the turbulence in the cylinder. When the turbulence in the cylinder increases, the flame propagates more rapidly, which results in decrease in the first-half combustion period. Thus, the engine rotation speed is also a parameter correlated with the turbulence in the cylinder. For this reason, it is preferable that the first-half combustion period is calculated by being multiplied by a correction coefficient based on the engine rotation speed (e.g., the correction coefficient of the engine rotation speed). In this way, it is possible to calculate the first-half combustion period further reflecting the influence of the turbulence in the cylinder, which sufficiently ensures the accuracy in the estimation of the first-half combustion period as well as ensures reliability of the heat generation rate waveform calculated using the first-half combustion period.

It is preferable that examples of the correction coefficient based on the engine rotation speed include an exponential function of the engine rotation speed with a value depending on a tumble ratio as exponent. The tumble ratio highly affects the turbulence in the cylinder together with the engine rotation speed. Thus, by using, as the correction coefficient based on the engine rotation speed, the exponential function of the engine rotation speed with the value depending on the tumble ratio as exponent, it is possible to calculate the first-half combustion period further reflecting the influence of the turbulence in the cylinder, which sufficiently ensures the accuracy in the estimation of the first-half combustion period.

Examples of the specific method for calculating the first-half combustion period include a method including the following steps: setting a virtual heat generation rate maximum time; and calculating repeatedly by changing the virtual heat generation rate maximum time so as to determine whether the virtual first-half combustion period that is obtained according to the physical quantity at the virtual heat generation rate maximum time coincides with the period from the actual ignition time to the virtual heat generation rate maximum time. That is, the virtual heat generation rate maximum time is set, and the virtual first-half combustion period between the ignition time obtained according to the actual spark time and the virtual heat generation rate maximum time is compared with an estimated first-half combustion period based on the physical quantity at the virtual heat generation rate maximum time so as to calculate a true first-half combustion period as the estimated first-half combustion period that coincides with the virtual first-half combustion period. Thus, the heat generation rate waveform is calculated using the true first-half combustion period. In this way, it is possible to approximate the virtual heat generation rate maximum time to the true heat generation rate maximum time. Accordingly, it is possible to correctly obtain the heat generation rate maximum time to estimate the first-half combustion period, which results in the calculation of the first-half combustion period with a high accuracy.

Examples of the heat generation rate waveform calculated using the above calculated first-half combustion period include a triangular waveform with a crank angle period from the ignition of the air-fuel mixture to combustion completion as a base and the heat generation rate at the heat generation rate maximum time as an apex. By approximating the heat generation rate waveform by the triangular waveform, the base of the triangle, which expresses the heat generation rate from the ignition time to the heat generation rate maximum time, is defined as the first-half combustion period.

It is preferable that the triangular waveform is produced under the condition that the first-half combustion period is not determined by at least one of the engine load rate, the air-fuel ratio, the exhaust gas recirculation (EGR) rate and the oil-water temperature, but determined mainly by the in-cylinder volume (a parameter correlated with the turbulence in the cylinder) and the engine rotation speed (also a parameter correlated with the turbulence in the cylinder) at the heat generation rate maximum time. That is, even when the engine load rate, the air-fuel ratio, the EGR rate and the oil-water temperature change, the first-half combustion period does not change, thus the triangular waveform can be produced under the condition that the change in the first-half combustion period corresponds to the influence of the turbulence in the cylinder. In this way, it is possible to reduce man-hours to produce the heat generation rate waveform.

From another standpoint, the present invention is directed to the method for calculating the heat generation rate waveform of a spark-ignition internal combustion engine. The method includes the steps of: defining, within the combustion period of the air-fuel mixture, the period from the ignition time to the heat generation rate maximum time where the heat generation rate is maximum as the first-half combustion period that is one of characteristic values of the heat generation rate waveform; estimating the first-half combustion period based on the physical quantity at the heat generation rate maximum time; and calculating the heat generation rate waveform using the estimated first-half combustion period.

Effects of Invention

In the present invention, the first-half combustion period from the ignition time of the air-fuel mixture to the heat generation rate maximum time where the heat generation rate is maximum is used as one of the characteristic values of the heat generation rate waveform of the internal combustion engine, and the first-half combustion period is estimated based on the physical quantity at the heat generation rate maximum time. Thus, it is possible to reduce man-hours to produce the heat generation rate waveform, and to simply estimate and evaluate the first-half combustion period while ensuring a required accuracy, without producing the entire heat generation rate waveform.

BRIEF DESCRIPTION OF DRAWINGS

FIG. 9(a) indicates the case in which the spark time SA is before the top dead center (BTDC), while FIG. 9(b) indicates the case in which the spark time SA is after the top dead center (ATDC).

MODES FOR CARRYING OUT INVENTION

Hereinafter, embodiments of the present invention will be described with reference to the drawings. In this embodiment, the present invention is applied to a heat generation rate waveform calculation device for calculating (producing) a heat generation rate waveform of a vehicle gasoline engine (spark ignition engine).

Figure 1:
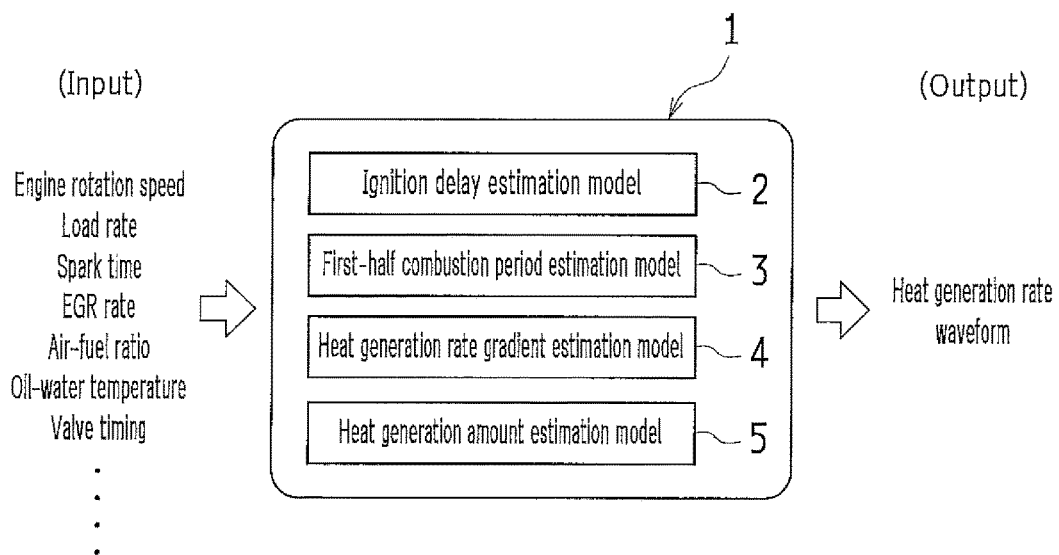
FIG. 1 is a diagram indicating a configuration of a heat generation rate waveform calculation device and its input/output information according to an embodiment.

FIG. 1 is a diagram indicating a configuration of a heat generation rate waveform calculation device 1 and its input/output information according to this embodiment. To the heat generation rate waveform calculation device 1, various pieces of information such as an engine state quantity, a control quantity of control parameters and a physical quantity are input. Examples of the above input information include an engine rotation speed, a load rate, a spark time, an EGR rate, an air-fuel ratio, an oil-water temperature, and an opening/closing timing (valve timing) of each intake/exhaust valve. Also, the heat generation rate waveform calculation device 1 estimates various characteristic values of a heat generation rate waveform based on each piece of input information, using estimation parts 2 to 5 in which respective estimation models are stored, and outputs the heat generation rate waveform produced using the various characteristic values.

—Estimation Part of Each Characteristic Value of Heat Generation Rate Waveform—

The heat generation rate waveform calculation device 1 includes: an ignition delay estimation part 2 that stores an ignition delay estimation model; a first-half combustion period estimation part 3 that stores a first-half combustion period estimation model; a heat generation rate gradient estimation part 4 that stores a heat generation rate gradient estimation model; and a heat generation amount estimation part 5 that stores a heat generation amount estimation model. The above estimation parts estimate, respectively, an ignition delay, a first-half combustion period, a heat generation rate gradient, and a heat generation amount as the characteristic values of the heat generation rate waveform.

The ignition delay estimation part 2 estimates a period (hereinafter referred to as "ignition delay period") from the time where an air-fuel mixture is sparked by an ignition plug of an engine (hereinafter referred to as "spark time", i.e., from the time where a spark discharge is performed between electrodes of the ignition plug) to the time where the air-fuel mixture is ignited by the spark and an initial flame kernel is formed (hereinafter referred to as "ignition time"), using the ignition delay estimation model. The ignition delay period is represented by a crank angle [CA]. In this embodiment, the ignition time is defined to be a time where the heat generation rate (heat generation amount per unit crank angle of the rotation of the crank shaft) reaches 1[J/CA] after the ignition time. The above value is not limited thereto and may be appropriately set. For example, the ignition time may be set to the time where the heat generation amount after the spark time reaches a predetermined rate (e.g., 5%) with respect to the total heat generation amount. Furthermore, the ignition time may be defined based on a time where the rate of the heat generation amount with respect to the total heat generation amount reaches a predetermined value (e.g., a crank angle position at the time where the rate reaches 10%) and a time where the rate of the heat generation amount reaches another predetermined value (e.g., a crank angle position at the time where the rate reaches 50%). That is, a triangle (triangular waveform) that is approximated to the heat generation rate waveform during increase of the heat generation rate is produced based on these crank angle positions and the rates of the heat generation amount, so that the ignition time is defined based on the triangular waveform. Also, the general shape of the heat generation rate waveform during increase of the heat generation rate may be applied to produce the heat generation rate waveform so that the above relationship between the crank angle position and the rate of the heat generation amount is established, thus, the ignition time may be defined based on the above heat generation rate waveform. The above respective values are not limited thereto, and may be appropriately set.

The first-half combustion period estimation part 3 estimates, in the combustion period of the air-fuel mixture, the first-half combustion period from the ignition time to a time where the heat generation rate is maximum according to growth of the flame kernel (i.e., a time where the heat generation rate is maximum within the period from the spark time to the combustion completion time), using the first-half combustion period estimation model. Hereinafter, the time where the heat generation rate is maximum is referred to as "heat generation rate maximum time". The heat generation rate maximum time and the first-half combustion period are respectively represented by the crank angle [CA].

The heat generation rate gradient estimation part 4 estimates an average increase rate of the heat generation rate (heat generation rate gradient) relative to changes in the crank angle in the first-half combustion period, i.e., the period from the ignition time to the heat generation rate maximum time, using the heat generation rate gradient estimation model. In this embodiment, as described below with reference to FIG. 2, the triangular waveform approximated to the heat generation rate waveform is produced. The heat generation rate gradient estimation part 4 is to estimate a gradient of the oblique side that represents the heat generation rate from the ignition time to the heat generation rate maximum time in the triangular waveform. The unit of the gradient of the heat generation rate is represented by $[J/CA^2]$.

The heat generation amount estimation part 5 estimates the heat generation amount generated by combustion of the air-fuel mixture (i.e., heat generation amount generated throughout the entire combustion period, which is an integrated value of the heat generation rate in the period from the spark time to the combustion completion time) using the heat generation amount estimation model. The unit of the heat generation amount is represented by [J].

By respective estimation operations in the estimation parts 2 to 5, the characteristic values of the heat generation rate waveform, i.e., the ignition delay, the first-half combustion period, the heat generation rate gradient and the heat generation amount are obtained. Then, the heat generation rate waveform is produced using these characteristic values. Thus produced heat generation rate waveform is the output of the heat generation rate waveform calculation device 1.

Figure 3:
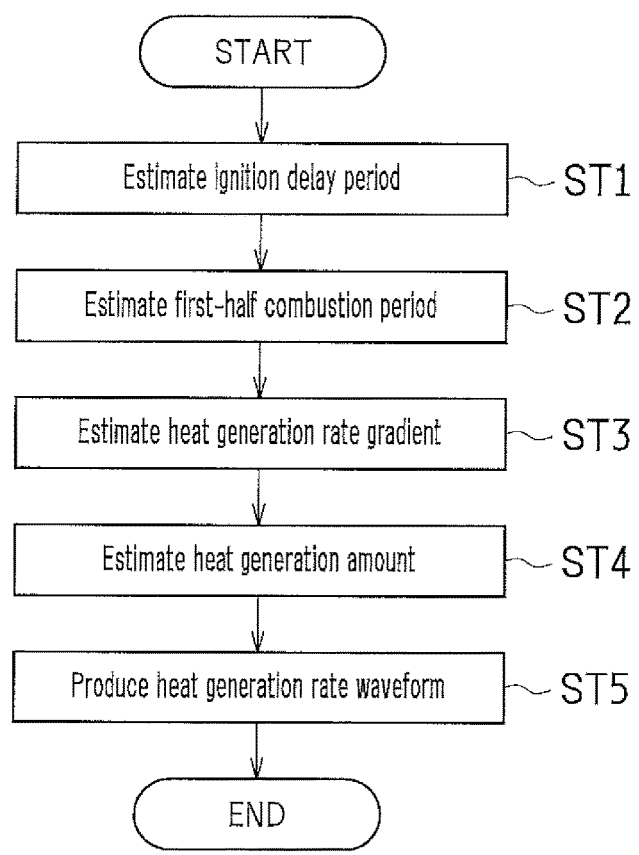
FIG. 3 is a flowchart indicating steps of producing the heat generation rate waveform performed by the heat generation rate waveform calculation device.

Thus, in the heat generation rate waveform calculation device 1 according to this embodiment, as shown in the flowchart of FIG. 3, the following steps are sequentially performed: an operation to estimate the ignition delay period by the ignition delay estimation part 2 (step ST1); an operation to estimate the first-half combustion period by the first-half combustion period estimation part 3 (step ST2); an operation to estimate heat generation rate gradient by the heat generation rate gradient estimation part 4 (step ST3); and an operation to estimate the heat generation amount by the heat generation amount estimation part 5 (step ST4). Then, an operation to produce the heat generation rate waveform using the estimated characteristic values is performed (step ST5).

Figure 2:
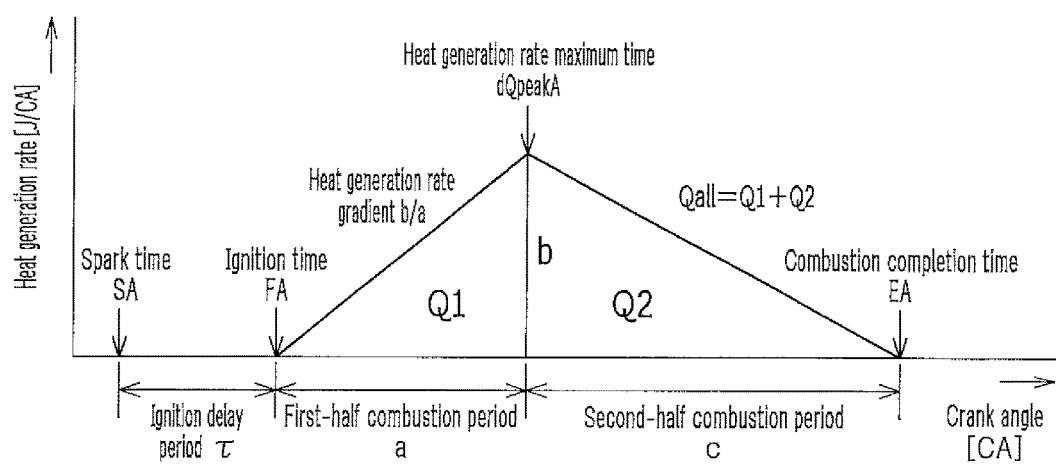
FIG. 2 is a graph indicating one example of a heat generation rate waveform that is output from the heat generation rate waveform calculation device.

FIG. 2 indicates one example of the heat generation rate waveform that is produced using the characteristic values estimated by the estimation parts 2 to 5 and that is output from the heat generation rate waveform calculation device 1. In FIG. 2, the time SA represents the spark time, and the time FA represents the ignition time. Therefore, the period $\tau$ in the graph represents the ignition delay period. Also, the time dQpeakA represents the heat generation rate maximum time, and the heat generation rate at the heat generation rate maximum time dQpeakA is represented by b in the graph. That is, the heat generation rate b represents the maximum heat generation rate in the combustion period. Also, the period a from the ignition time FA to the heat generation rate maximum time dQpeakA represents the first-half combustion period. Thus, the gradient of the heat generation rate in the first-half combustion period a is represented by b/a. Furthermore, the period c from the heat generation rate maximum time dQpeakA to the combustion completion time EA represents a second-half combustion period. In the graph, Q1 represents the heat generation amount in the first-half combustion period a, and Q2 represents the heat generation amount in the second-half combustion period c. Thus, the heat generation amount (total heat generation amount $Q_{all}$) generated throughout the entire combustion period is represented as a sum of the heat generation amount Q1 and the heat generation amount Q2.

In other words, the heat generation rate waveform calculation device 1 of this embodiment approximates the heat generation rate waveform by the triangular waveform with the crank angle period from the ignition of the air-fuel mixture to the combustion completion (i.e., from FA to EA in the graph) as a base and the heat generation rate b at the heat generation rate maximum time dQpeakA as an apex. In this case, the base of the triangle, which represents the heat generation rate from the ignition time FA to the heat generation rate maximum time dQpeakA, is the first-half combustion period a. In this embodiment, the system, control and adaptive values are reviewed when designing an engine, using the heat generation rate waveform that is output from the heat generation rate waveform calculation device 1.

Hereinafter, estimation processing in each of the estimation parts 2 to 5 will be specifically described.

—Ignition Delay Estimation Part—

As described above, the ignition delay estimation part 2 estimates the ignition delay period $\tau$ from the spark time SA to the ignition time FA.

The processing for estimating the ignition delay period $\tau$ is performed by the ignition delay estimation part 2 as described below.

The ignition delay period $\tau$ is estimated using either of the following estimations (1) and (2) (i.e., these expressions correspond to the ignition delay estimation model).

[Expression 1]

$$\tau = C_1 \times \rho_{fuel@SA}{}^{\chi} \times Ne^{\delta} \quad (1)$$

[Expression 2]

$$\tau = C_2 \times \rho_{fuel@FA}{}^{\phi} \times Ne^{\psi} \quad (2)$$

In the above expression, $\rho_{fuel@SA}$ represents an in-cylinder fuel density at the spark time SA (i.e., in-cylinder fuel amount [mol]/in-cylinder volume [L] at spark time), while $\rho_{fuel@FA}$ represents an in-cylinder fuel density at the ignition time FA (i.e., in-cylinder fuel amount [mol]/in-cylinder volume [L] at ignition time). Ne represents the engine rotation speed. $C_1$, $C_2$, $\chi$, $\delta$, $\phi$, $\Psi$ represent coefficients respectively identified by experiments and the like.

The above expressions (1) and (2) hold under the condition that the air-fuel ratio is the theoretical air-fuel ratio, the EGR rate equals zero, the warming-up operation of the engine is finished (i.e., the oil-water temperature is a predetermined value or more), and the opening/closing timing of the intake valve is fixed.

The expression (1) is to calculate the ignition delay period $\tau$ when the air-fuel mixture is ignited on an advance side (BTDC) of the time where the piston reaches the compression top dead center (TDC) (hereinafter referred to as "BTDC ignition"). The expression (2) is to calculate the ignition delay period $\tau$ when the air-fuel mixture is ignited on a delay side (ATDC) of the time where the piston reaches the compression top dead center (TDC) (hereinafter referred to as "ATDC ignition").

As shown in the expressions, the ignition delay period $\tau$ is calculated by the arithmetic expression with the in-cylinder fuel density $\rho_{fuel}$ and the engine rotation speed at a predetermined time Ne as variables.

The reason why the ignition delay period $\tau$ can be calculated by the above arithmetic expressions will be described below.

Figure 4:
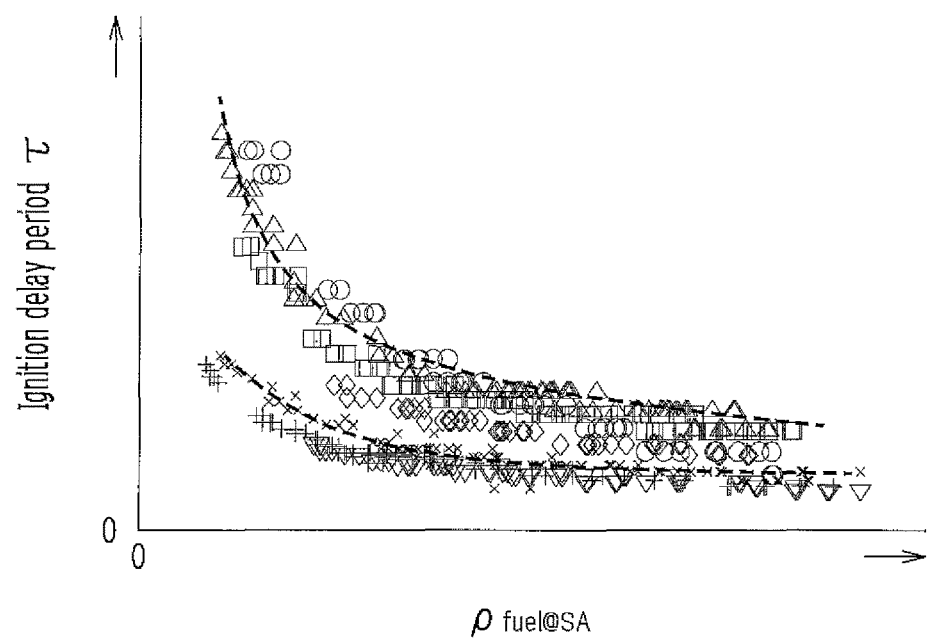
FIG. 4 is a graph indicating measured results, by experiments, of changes in an ignition delay period τ relative to changes in an in-cylinder fuel density $\rho_{fuel@SA}$ at a spark time SA in the case of ignition before the compression top dead center (hereinafter referred to as "BTDC ignition").

FIG. 4 is a graph indicating measured results, by experiments, of changes in the ignition delay period $\tau$ relative to changes in the in-cylinder fuel density $\rho_{fuel@SA}$ at the spark time SA in the case of the BTDC ignition. These experiments were performed under the condition that the air-fuel ratio was the theoretical air-fuel ratio, the EGR rate equaled zero, the warming-up operation of the engine was finished (i.e., the oil-water temperature was the predetermined value or more), and the opening/closing timing of the intake valve was fixed. Also, in FIG. 4, the engine rotation speed Ne increases in the following order: "○"; "△"; "□"; "◇"; "x"; "+"; and "∇". For example, "○" represents 800 rpm, "△" represents 1000 rpm, "□" represents 1200 rpm, "◇" represents 1600 rpm, "x" represents 2400 rpm, "+" represents 3200 rpm and "∇" represents 3600 rpm.

As shown in FIG. 4, in the case of the BTDC ignition, the in-cylinder fuel density $\rho_{fuel@SA}$ at the spark time SA is correlated with the ignition delay period $\tau$ for each engine rotation speed Ne, That is, each correlation can substantially be expressed by a corresponding curve. In FIG. 4, for each case in which the engine rotation speed Ne is 1000 rpm and 2400 rpm, the corresponding correlation between the in-cylinder fuel density $\rho_{fuel@SA}$ at the spark time SA and the ignition delay period $\tau$ is expressed by one curve.

As shown in FIG. 4, as the in-cylinder fuel density $\rho_{fuel@SA}$ at the spark time SA increases, the ignition delay period $\tau$ decreases. This is probably due to the fact that as the fuel density $\rho_{fuel@SA}$ increases, the number of fuel molecules around the ignition plug increases, which results in rapid growth of the flame kernel after the ignition plug sparks. Also, the engine rotation speed Ne affects the ignition delay period $\tau$. That is, as the engine rotation speed Ne increases, the ignition delay period $\tau$ decreases. This is probably due to the fact that as the engine rotation speed Ne increases, a turbulence in flow of the air-fuel mixture (hereinafter simply referred to as "turbulence") in the cylinder increases, which results in rapid growth of the flame kernel. Thus, the in-cylinder fuel density $\rho_{fuel@SA}$ and the engine rotation speed Ne at the spark time SA are parameters that affect the ignition delay period τ.

Figure 5:
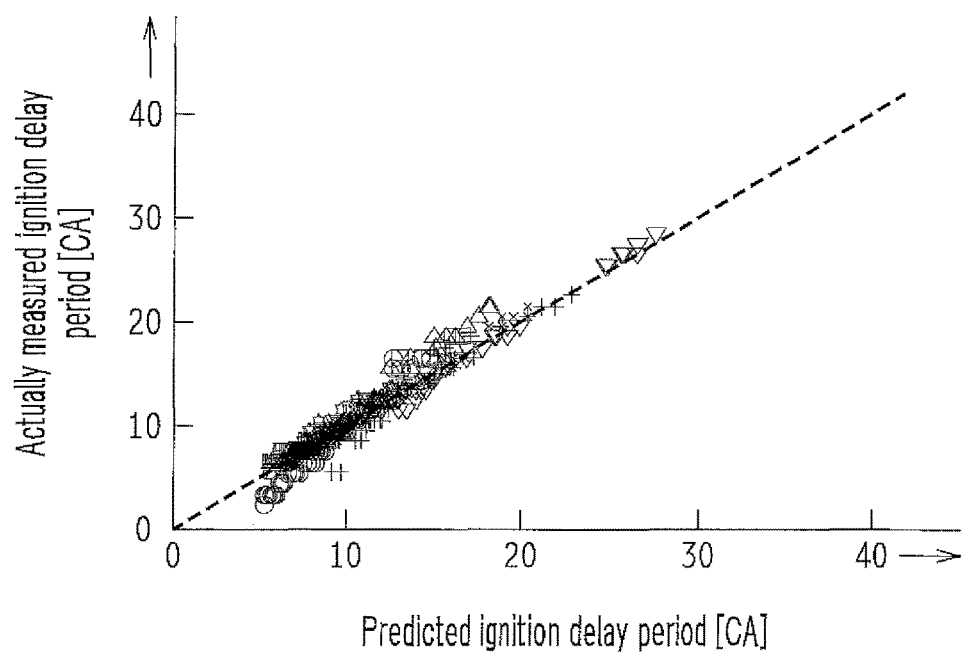
FIG. 5 is a graph indicating results obtained by verifying the relationship between a predicted ignition delay period calculated by an expression (1) and an actually measured ignition delay period measured by an actual machine.

FIG. 5 is a graph indicating results obtained by verifying the relationship between a predicted ignition delay period calculated by the expression (1) and an actually measured ignition delay period measured by an actual machine. In order to obtain the predicted ignition delay period, a prediction expression is used, which is obtained by identifying each coefficient $C_1$, χ, and δ in the expression (1) according to each engine operation condition. In FIG. 5, the engine rotation speed Ne increases in the following order: "○"; "△"; "□"; "◇"; "x"; "+"; "∇"; and "☆". For example, "○" represents 800 rpm, "△" represents 1000 rpm, "□" represents 1200 rpm, "◇" represents 1600 rpm, "x" represents 2000 rpm, "+" represents 2400 rpm, "∇" represents 3200 rpm and "☆" represents 3600 rpm.

As clearly shown in FIG. 5, the predicted ignition delay period substantially coincides with the actually measured ignition delay period. Thus, it can be clearly seen that the ignition delay period in the case of the BTDC ignition is calculated with a high accuracy by the expression (1).

Figure 6:
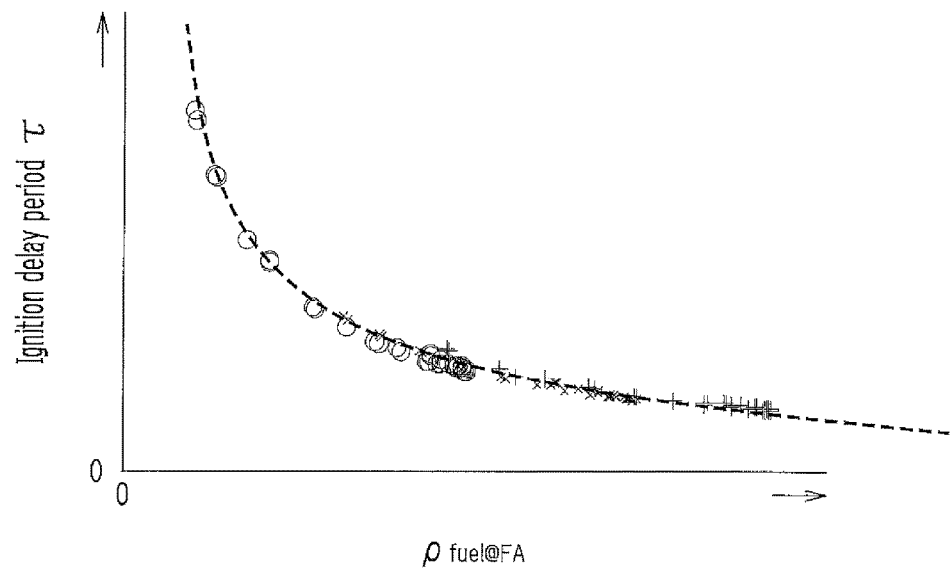
FIG. 6 is a graph indicating measured results, by experiments, of changes in the ignition delay period τ relative to changes in the in-cylinder fuel density $\rho_{fuel@FA}$ at an ignition time FA in the case of ignition after the compression top dead center (hereinafter referred to as "ATDC ignition").

FIG. 6 is a graph indicating measured results, by experiments, of changes in the ignition delay period τ relative to changes in the in-cylinder fuel density $\rho_{fuel@FA}$ at the ignition time FA in the case of the ATDC ignition. These experiments were performed under the condition that the engine rotation speed was fixed, the air-fuel ratio was the theoretical air-fuel ratio, the EGR rate equaled zero, the warming-up operation of the engine was finished (i.e., the oil-water temperature was the predetermined value or more), and the opening/closing timing of the intake valve was fixed. Also, in FIG. 6, the load rate increases in the following order: "○"; "x"; "+"; and "△". For example, "○" represents 20% load rate, "x" represents 30% load rate, "+" represents 40% load rate and "△" represents 50% load rate.

As shown in FIG. 6, in the case of the ATDC ignition, the in-cylinder fuel density $\rho_{fuel@FA}$ at the ignition time FA is correlated with the ignition delay period τ regardless of the load rate (irrespective of the load rate). That is, the correlation can substantially be expressed by one curve.

As shown in FIG. 6, as the in-cylinder fuel density $\rho_{fuel@FA}$ at the ignition time FA increases, the ignition delay period τ decreases. As described above, this is probably due to the fact that as the fuel density $\rho_{fuel@FA}$ increases, the number of fuel molecules around the ignition plug increases, which results in rapid growth of the flame kernel after the ignition plug sparks. Thus, the in-cylinder fuel density $\rho_{fuel@FA}$ at the ignition time FA is a parameter that affects the ignition delay period τ. Also, similarly to the above, the engine rotation speed Ne is considered to be a parameter that affects the ignition delay period τ.

Figure 7:
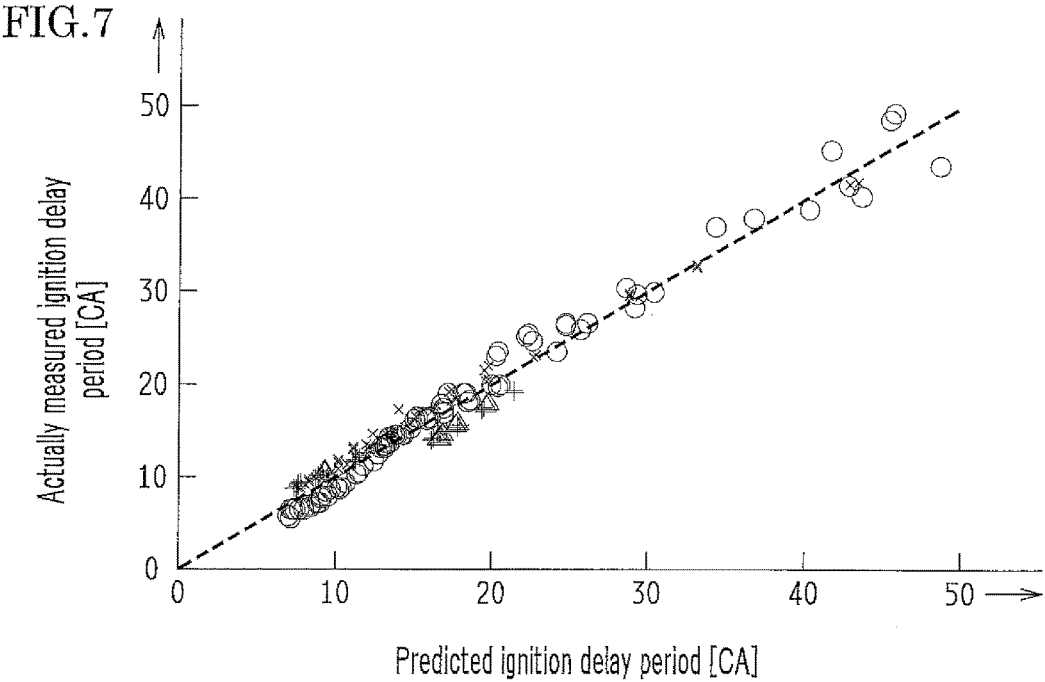
FIG. 7 is a graph indicating results obtained by verifying the relationship between a predicted ignition delay period calculated by an expression (2) and an actually measured ignition delay period measured by an actual machine.

FIG. 7 is a graph indicating results obtained by verifying the relationship between the predicted ignition delay period calculated by the expression (2) and the actually measured ignition delay period measured by an actual machine. In order to obtain the predicted ignition delay period, a prediction expression is used, which is obtained by identifying each coefficient $C_2$, φ, and Ψ in the expression (2) according to each engine operation condition. In FIG. 7, the engine rotation speed Ne increases in the following order: "○"; "x"; "+"; and "△". For example, "○" represents 800 rpm, "x" represents 1200 rpm, "+" represents 3600 rpm and "△" represents 4800 rpm.

As clearly shown in FIG. 7, the predicted ignition delay period substantially coincides with the actually measured ignition delay period. Thus, it can be clearly seen that the ignition delay period in the case of the ATDC ignition is calculated with a high accuracy by the expression (2).

From the above-described new knowledge, the inventor of the present invention derived the above expressions (1) and (2).

Hereinafter, the reason why the ignition delay period τ is calculated by being classified according to the ignition time will be described. That is, the reason why the BTDC ignition and the ATDC ignition are classified to calculate the respective ignition delay periods τ using the different arithmetic expressions (the above expressions (1) and (2)).

Figure 8:
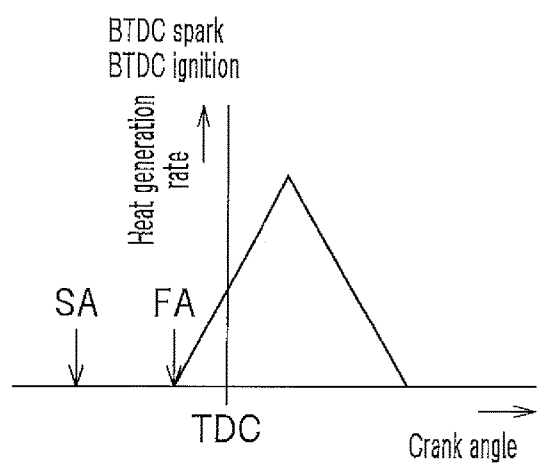
FIG. 8 is a graph indicating the spark time SA and the heat generation rate waveform in the BTDC ignition.

First, in the case of the BTDC ignition, the spark time SA is also on the advance side (BTDC) of the time where the piston reaches the compression top dead center, as shown in FIG. 8 (Figure indicating the spark time SA and the heat generation rate waveform). In this case, after the spark time SA passes, the piston moves toward the compression top dead center. Thus, the in-cylinder volume decreases, which results in the fuel density $\rho_{fuel}$ increasing. For this reason, regarding the fuel density $\rho_{fuel}$, the fuel density $\rho_{fuel@SA}$ at the spark time SA is smaller than the fuel density $\rho_{fuel@FA}$ at the ignition time FA. Thus, it is possible to obtain the ignition delay period τ with a high accuracy by multiplying the fuel density $\rho_{fuel@SA}$ at the spark time SA, which is correlated with the maximum value of the ignition delay period (the longest predicted ignition delay period), by the various coefficients previously identified.

Figure 9:
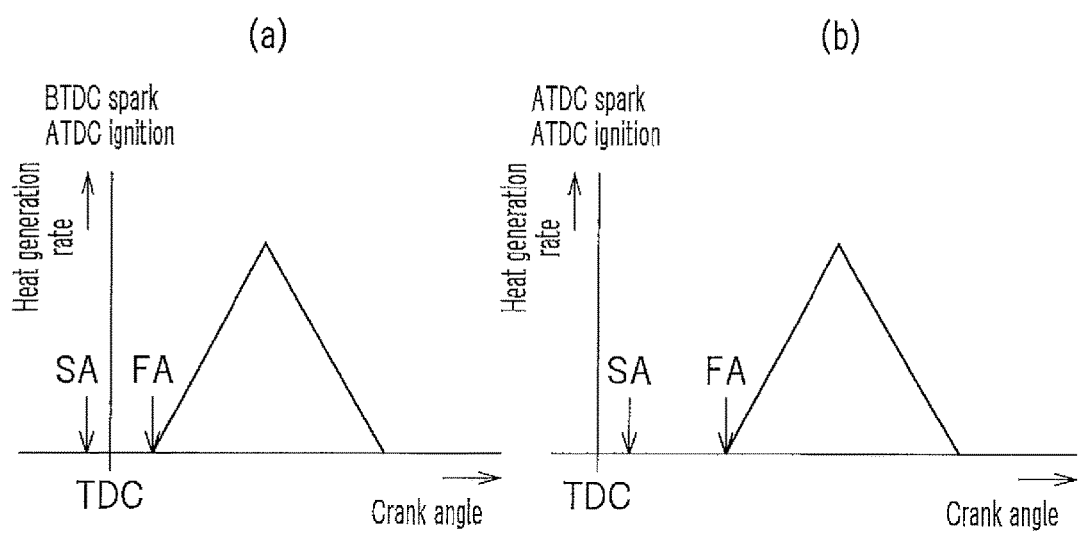
FIG. 9 are graphs indicating the spark time SA and the heat generation rate waveform in the ATDC ignition.

On the other hand, in the case of the ATDC ignition, the spark time SA is on the advance side (BTDC) of the time where the piston reaches the compression top dead center (see FIG. 9(a)) or on the delay side (ATDC) (see FIG. 9(b)), as shown in FIG. 9 (Figures indicating the spark time SA and the heat generation rate waveform). In these cases, after the ignition time FA passes, the piston moves toward the compression bottom dead center. Thus, the in-cylinder volume increases, which results in the fuel density $\rho_{fuel}$ decreasing. For this reason, regarding the fuel density $\rho_{fuel}$, the fuel density $\rho_{fuel@FA}$ at the ignition time FA is likely to be smaller than the fuel density $\rho_{fuel@SA}$ at the spark time SA. Thus, it is possible to obtain the ignition delay period τ with a high accuracy by multiplying the fuel density $\rho_{fuel@FA}$ at the ignition time FA, which is correlated with the maximum value of the ignition delay period (the longest predicted ignition delay period), by the various coefficients previously identified.

Also, the steps of determining which expression out of the expressions (1) and (2) is used (i.e., steps of determining into which the ignition time falls, the BTDC ignition or the ATDC ignition), and the steps of calculating the ignition delay period (true ignition delay period, described later) are described as follows. A virtual ignition time is set so as to obtain the in-cylinder volume at the virtual ignition time. Since the in-cylinder volume can be geometrically obtained from the crank angle position (piston position) corresponding to the virtual ignition time, the in-cylinder volume is uniquely determined upon the virtual ignition time. Then, the fuel density is obtained from the in-cylinder volume and the fuel injection amount. When the virtual ignition time is set as the BTDC ignition, the fuel density and the engine rotation speed at the virtual ignition time are substituted into the expression (1) so as to calculate an estimated ignition delay period. On the other hand, when the virtual ignition time is set as the ATDC ignition, the fuel density and the engine rotation speed at the virtual ignition time are substituted into the expression (2) so as to calculate the estimated ignition delay period. Thus, the time that is advanced by the above-calculated estimated ignition delay period is set as a virtual spark time relative to the virtual ignition time. Here, the virtual spark time is compared with the actual spark time (spark time as the input information). When the virtual spark time does not coincide with the actual spark time, the virtual ignition time is changed. For example, the virtual ignition time is changed to the delay side. Then, the fuel density and the engine rotation speed at the virtual ignition time are substituted into the expression (1) or (2) (i.e., when the virtual ignition time is set as the BTDC ignition, the above values are substituted into the expression (1), while the virtual ignition time is set as the ATDC ignition, the above values are substituted into the expression (2)), so that the estimated ignition delay period is calculated. Thus, the virtual spark time is obtained, and compared with the actual spark time (spark time as the input information). The above proceeding is repeatedly performed, and the virtual ignition time in the case that the virtual spark time coincides with the actual spark time can be obtained as the true ignition time. At the same time (where the true ignition time is obtained), the estimated ignition delay period calculated by the expression (1) or (2) can also be obtained as the true ignition delay period. When the true ignition time is BTDC (BTDC ignition), the obtained ignition time may be once again substituted into the expression (1) so as to calculate the ignition delay period τ. When the true ignition time is ATDC (ATDC ignition), the obtained ignition time may be once again substituted into the expression (2) so as to calculate the ignition delay period τ.

The above steps can also be described as follows. The period between the actual spark time and the virtual ignition time (i.e., virtual ignition delay period in the case of the ignition at the virtual ignition time) is compared with the estimated ignition delay period calculated (estimated) by the expression (1) or (2). When the above periods do not coincide with each other, the virtual ignition time is changed. After the estimated ignition delay period is calculated once again by the expression (1) or (2), the period between the actual spark time and the virtual ignition time (i.e., virtual ignition delay period) is compared with the estimated ignition delay period calculated by the expression (1) or (2). The above proceeding is repeatedly performed, thus the estimated ignition delay period in the case that the two periods coincide with each other (i.e., the virtual ignition delay period coincides with the estimated ignition delay period) is obtained as the true ignition delay period.

Thus, by estimating the ignition delay period τ by the ignition delay estimation part 2, it is possible to estimate the ignition delay period τ over the entire operation range of the engine.

When the ignition delay period τ is obtained as described above, it is possible to obtain the ignition time FA by adding the ignition delay period τ to the spark time SA.

—First-Half Combustion Period Estimation Part—

As described above, the first-half combustion period estimation part 3 estimates the first-half combustion period a from the ignition time FA to the heat generation rate maximum time dQpeakA.

The processing for estimating the first-half combustion period a is performed by the first-half combustion period estimation part 3 as described below.

The first-half combustion period a [CA] is estimated using the following expression (3) (i.e., the expression corresponds to the first-half combustion period estimation model).

[Expression 3]

$$a = C \times V_{@dQpeak}^{\alpha} \times Ne^{\beta} \qquad (3)$$

In the above expression, $V_{@dQpeak}$ represents the in-cylinder volume [L] as a physical quantity at the heat generation rate maximum time dQpeakA, which is also referred to as "in-cylinder volume at heat generation rate maximum time" hereinafter. Ne represents the engine rotation speed.

The above expression (3) holds under the condition that the opening/closing timing of the intake valve is fixed. Also, the above expression (3) holds without being affected by the load rate, the EGR rate, the air-fuel ratio and the oil-water temperature. That is, the expression (3) holds based on the fact that the first-half combustion period a is not affected by the load rate, the EGR rate, the air-fuel ratio and the oil-water temperature.

The reason why the first-half combustion period a can be calculated by the above expression (3) will be described below.

Figure 10:
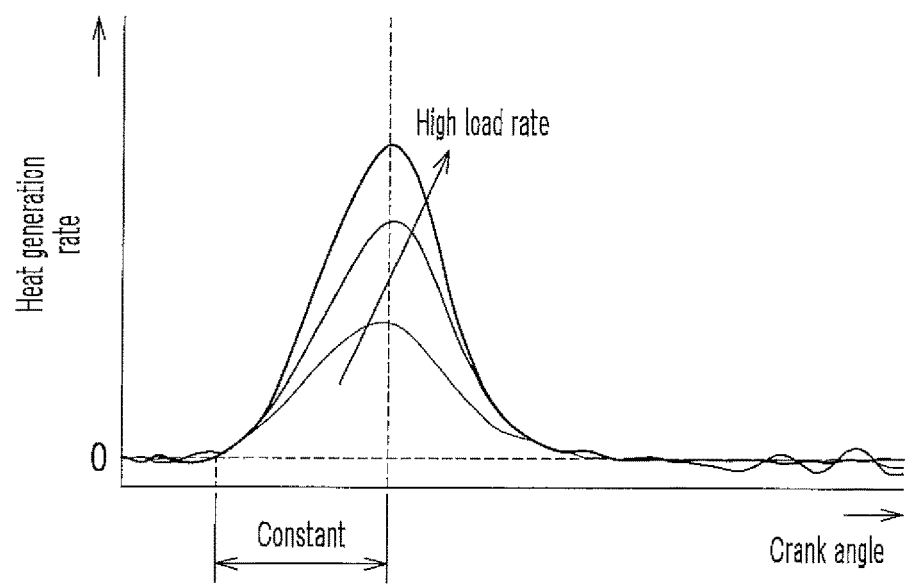
FIG. 10 is a graph indicating the heat generation rate waveforms obtained in respective engine operation states that differ from one another only in the load rate, by adjusting each spark time SA so that respective heat generation rate maximum times dQpeakA match with one another, the heat generation rate waveforms being indicated in a manner overlapping with one another.
Figure 11:
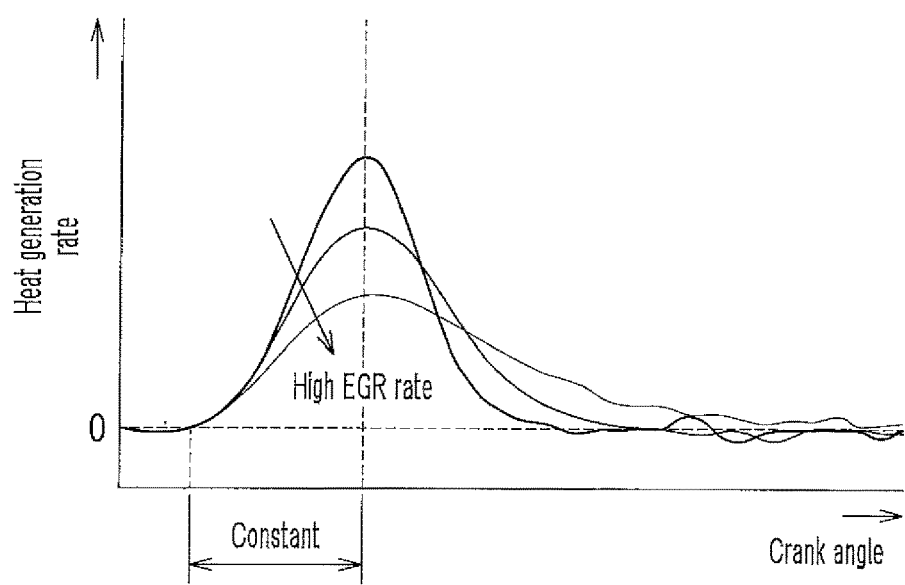
FIG. 11 is a graph indicating the heat generation rate waveforms obtained in respective engine operation states that differ from one another only in the exhaust gas recirculation (EGR) rate, by adjusting each spark time SA so that the respective heat generation rate maximum times dQpeakA match with one another, the heat generation rate waveforms being indicated in a manner overlapping with one another.
Figure 12:
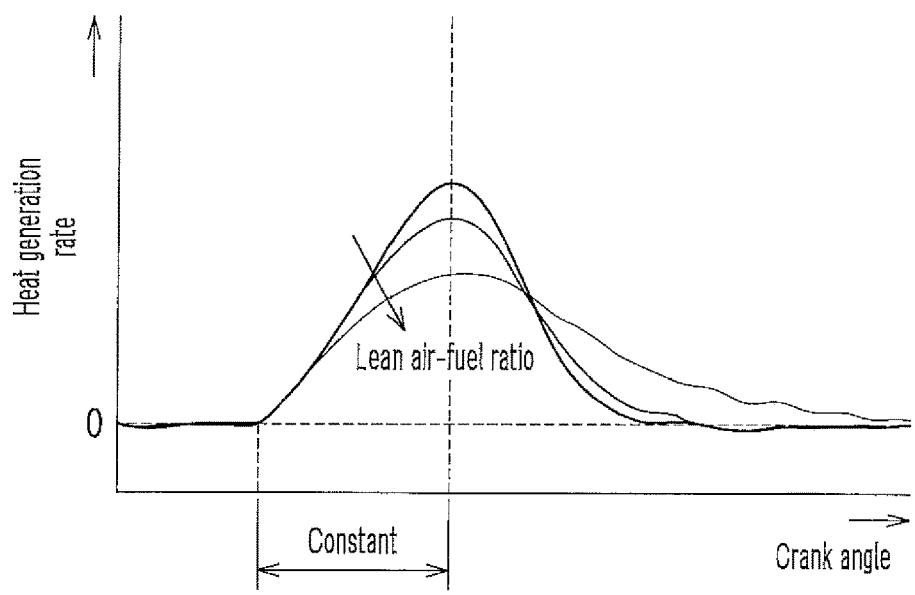
FIG. 12 is a graph indicating the heat generation rate waveforms obtained in respective engine operation states that differ from one another only in the air-fuel ratio, by adjusting each spark time SA so that the respective heat generation rate maximum times dQpeakA match with one another, the heat generation rate waveforms being indicated in a manner overlapping with one another.
Figure 13:
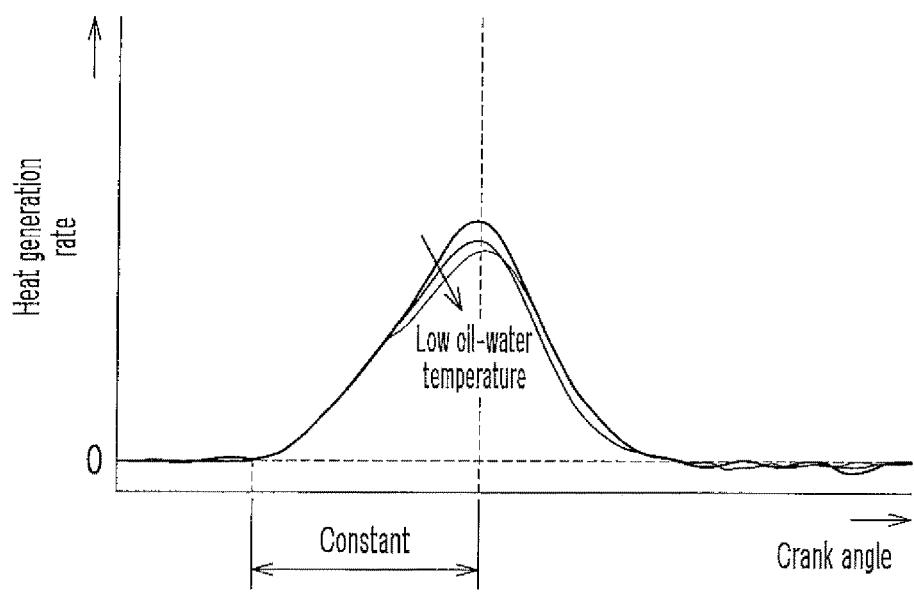
FIG. 13 is a graph indicating the heat generation rate waveforms obtained in respective engine operation states that differ from one another only in the oil-water temperature, by adjusting each spark time SA so that the respective heat generation rate maximum times dQpeakA match with one another, the heat generation rate waveforms being indicated in a manner overlapping with one another.

FIGS. 10 to 13 are graphs indicating the heat generation rate waveforms obtained in respective engine operation states that differ from one another, by adjusting each spark time SA so that the respective heat generation rate maximum times dQpeakA match with one another, the heat generation rate waveforms being indicated in a manner overlapping with one another. FIG. 10 indicates, in an overlapping manner, the heat generation rate waveforms obtained in the respective engine operation states that differ from one another only in the load rate. FIG. 11 indicates, in an overlapping manner, the heat generation rate waveforms obtained in the respective engine operation states that differ from one another only in the EGR rate. FIG. 12 indicates, in an overlapping manner, the heat generation rate waveforms obtained in the respective engine operation states that differ from one another only in the air-fuel ratio. Also, FIG. 13 indicates, in an overlapping manner, the heat generation rate waveforms obtained in the respective engine operation states that differ from one another only in the oil-water temperature during, for example, the warming-up operation of the engine.

As shown in FIGS. 10 to 13, the first-half combustion period a is maintained to be constant regardless of any changes in the load rate, the EGR rate, the air-fuel ratio and the oil-water temperature. Thus, it can be seen that the first-half combustion period a is not affected by the load rate, the EGR rate, the air-fuel ratio and the oil-water temperature.

Figure 14:
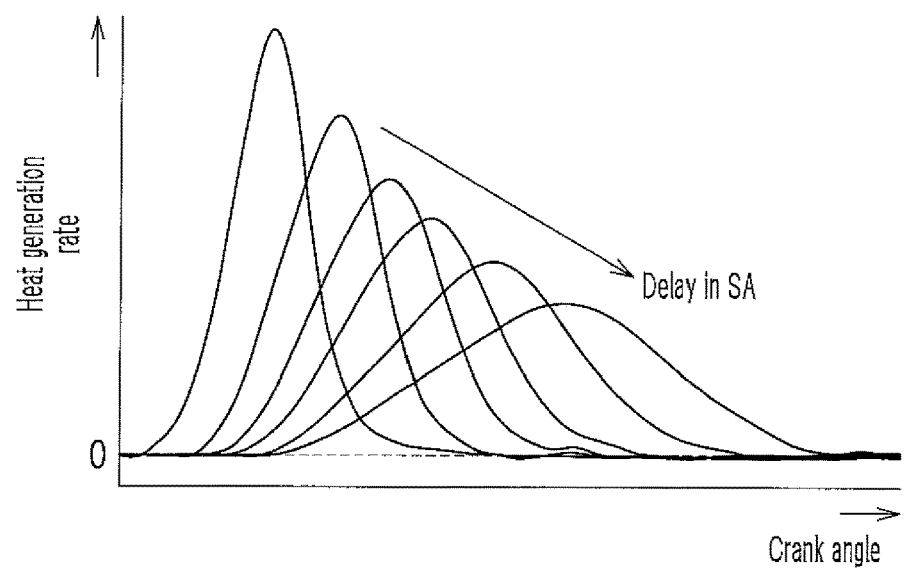
FIG. 14 is a graph indicating the heat generation rate waveforms obtained in the respective engine operation states that differ from one another in the spark time SA, the heat generation rate waveforms being indicated in a manner overlapping with one another.

In contrast, FIG. 14 is a graph indicating, in an overlapping manner, the heat generation rate waveforms obtained in the respective engine operation states that differ from one another in the spark time SA. As can be seen from FIG. 14, as the spark time SA is delayed, the first-half combustion period a increases.

Figure 15:
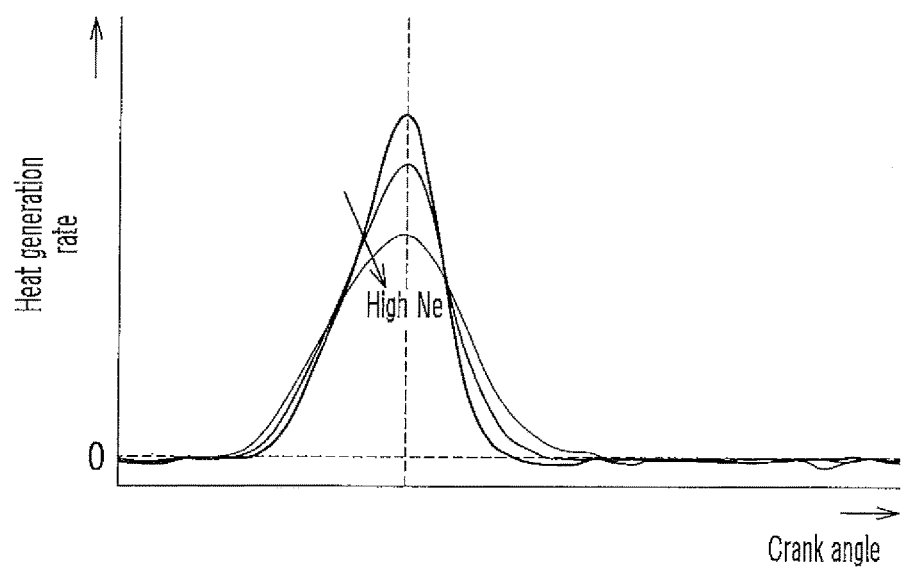
FIG. 15 is a graph indicating the heat generation rate waveforms obtained in the respective engine operation states that differ from one another only in the engine rotation speed Ne, by adjusting each spark time SA so that the respective heat generation rate maximum times dQpeakA match with one another, the heat generation rate waveforms being indicated in a manner overlapping with one another.

FIG. 15 is a graph indicating the heat generation rate waveforms obtained in the respective engine operation states that differ from one another only in the engine rotation speed Ne, by adjusting each spark time SA so that the respective heat generation rate maximum times dQpeakA match with one another, the heat generation rate waveforms being indicated in a manner overlapping with one another. As the engine rotation speed Ne increases, the crank rotation angle [CA] per unit time [ms] increases, which would lead to increase (on the axis of the crank angle) of the first-half combustion period a. However, in FIG. 15, the first-half combustion period a is almost unchanged although the engine rotation speed Ne changes. It is considered that there is any factor that shortens the first-half combustion period a as the engine rotation speed Ne increases. That is, apart from the increase of the first-half combustion period a caused by the fact that the crank rotation angle per unit time increases as the engine rotation speed Ne increases, there should be "another factor" that shortens the first-half combustion period a.

Thus, it can be seen that the first-half combustion period a is affected by the spark time SA and the engine rotation speed Ne.

The reason why the first-half combustion period a is affected by the spark time SA and the engine rotation speed Ne is considered to be influence of the spark time SA and the engine rotation speed Ne on the turbulence in the cylinder.

That is, in the case that the heat generation rate maximum time dQpeakA is on the delay side of the TDC, as the spark time SA is shifted to the delay side, the ignition time FA and the heat generation rate maximum time dQpeakA are shifted to the delay side. Thus, the in-cylinder volume at the heat generation rate maximum time dQpeakA (i.e., in-cylinder volume $V_{@dQpeak}$ at heat generation rate maximum time) increases while the turbulence in the cylinder reduces. When the turbulence in the cylinder reduces, the flame propagates more slowly, which results in increase in the first-half combustion period a. On the other hand, as the spark time SA is shifted to the advance side, the ignition time FA and the heat generation rate maximum time dQpeakA are shifted to the advance side. Thus, the in-cylinder volume $V_{@dQpeak}$ at heat generation rate maximum time reduces while the turbulence in the cylinder increases, which results in rapid flame propagation. Thus, the first-half combustion period a decreases.

Also, as the engine rotation speed Ne decreases, the flow rate of the air that flows from the intake system into the cylinder decreases, which leads to reduction in the turbulence in the cylinder. When the turbulence in the cylinder reduces, the flame propagates more slowly, which results in increase in the first-half combustion period a. On the other hand, as the engine rotation speed Ne increases, the flow rate of the air that flows from the intake system into the cylinder increases, which leads to increase in the turbulence in the cylinder. When the turbulence in the cylinder increases, the flame propagates more rapidly, which results in decrease in the first-half combustion period a. The above-mentioned "another factor (that shortens the first-half combustion period a)" means the rapid flame propagation caused by the fact that as the engine rotation speed Ne increases, the turbulence in the cylinder increases.

From the above-described new knowledge, the inventor of the present invention derived the above expression (3). In the expression (3), the in-cylinder volume, in particular the in-cylinder volume $V_{@dQpeak}$ at heat generation rate maximum time, which is a physical quantity correlated with the spark time SA that is a control quantity, is used as a variable. That is, as described above, as the spark time SA is shifted to the delay side, the heat generation rate maximum time dQpeakA is shifted to the delay side, which leads to increase in the in-cylinder volume $V_{@dQpeak}$. Therefore, the in-cylinder volume $V_{@dQpeak}$ at heat generation rate maximum time, which is a physical quantity correlated with the spark time SA, is used as a variable.

The steps of obtaining the in-cylinder volume $V_{@dQpeak}$ at heat generation rate maximum time, which is the variable in the expression (3), and the steps of calculating the first-half combustion period a are described as follows. A virtual heat generation rate maximum time is set so as to obtain the in-cylinder volume at the virtual heat generation rate maximum time. Since the in-cylinder volume can be geometrically obtained from the crank angle position (piston position) corresponding to the virtual heat generation rate maximum time, the in-cylinder volume is uniquely determined upon the virtual heat generation rate maximum time. Then, an estimated first-half combustion period is calculated by substituting the in-cylinder volume and the engine rotation speed at the virtual heat generation rate maximum time into the expression (3). Thus, the time that is advanced by the above-calculated estimated first-half combustion period is set as a virtual ignition time relative to the virtual heat generation rate maximum time. Since the above-described ignition delay estimation part 2 calculates the ignition delay period $\tau$, the ignition time FA can be calculated by adding the ignition delay period $\tau$ to the spark time SA. Here, the virtual ignition time is compared with the calculated ignition time FA. When the virtual ignition time does not coincide with the calculated ignition time FA, the virtual heat generation rate maximum time is changed. For example, the virtual heat generation rate maximum time is changed to the delay side. Then, the in-cylinder volume and the engine rotation speed at the virtual heat generation rate maximum time are substituted into the expression (3) so that the estimated first-half combustion period is calculated. Thus, the virtual ignition time is obtained, and compared with the calculated ignition time FA (obtained by adding, to the spark time SA, the ignition delay period $\tau$ calculated by the ignition delay estimation part 2). The above proceeding is repeatedly performed, and the virtual heat generation rate maximum time in the case that the virtual ignition time coincides with the calculated ignition time FA can be obtained as the true heat generation rate maximum time dQpeakA. At the same time (where the true heat generation rate maximum time dQpeakA is obtained), the estimated first-half combustion period calculated by the expression (3) can also be obtained as the true first-half combustion period. Also, the in-cylinder volume $V_{@dQpeak}$ at the true heat generation rate maximum time dQpeakA may be geometrically obtained and substituted into the expression (3) once again so as to calculate the first-half combustion period a.

The above steps can also be described as follows. The period between the ignition time FA (ignition time obtained based on the actual ignition time) and the virtual heat generation rate maximum time (i.e., the virtual first-half combustion period) is compared with the estimated first-half combustion period calculated (estimated) by the expression (3) (i.e., the estimated first-half combustion period based on the physical quantity at the virtual heat generation rate maximum time). When the above periods do not coincide with each other, the virtual heat generation rate maximum time is changed. After the estimated first-half combustion period is calculated once again by the expression (3), the period between the ignition time FA and the virtual heat generation rate maximum time (i.e., virtual first-half combustion period) is compared with the estimated first-half combustion period calculated by the expression (3). The above proceeding is repeatedly performed, thus the estimated first-half combustion period in the case that the two periods coincide with each other (i.e., the virtual first-half combustion period coincides with the estimated first-half combustion period) is obtained as the true first-half combustion period a.

The respective coefficients in the expression (3) are specifically described. C and $\alpha$ are identified based on experiments and the like. $\beta$ is a value depending on the tumble ratio in the cylinder, which increases as the tumble ratio increases. Also, $\beta$ may be set as the identified value based on experiments and the like. Also, these coefficients may be identified according to changes in the opening/closing timing of the intake valve. In this way, the first-half combustion period a is calculated by the expression (3) that is based on the in-cylinder volume $V_{@dQpeak}$ at heat generation rate maximum time and multiplied by the exponential function (correction coefficient) of the engine rotation speed Ne with the value β depending on the tumble ratio as exponent.

Figure 16:
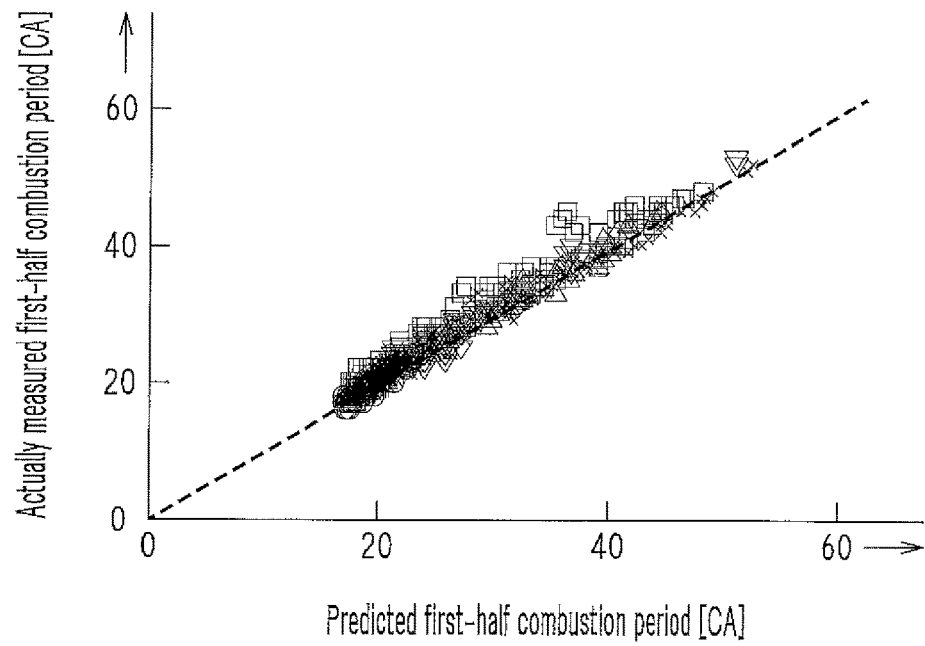
FIG. 16 is a graph indicating results obtained by verifying the relationship, in an engine, between a predicted first-half combustion period calculated by an expression (3) and an actually measured first-half combustion period measured by an actual machine.
Figure 17:
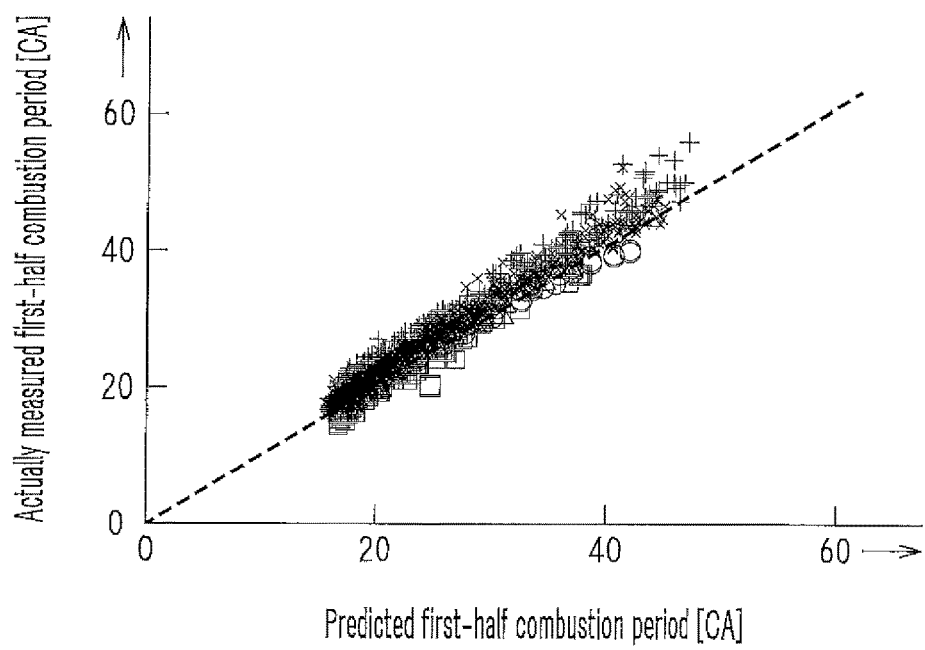
FIG. 17 is a graph indicating results obtained by verifying the relationship, in another engine, between the predicted first-half combustion period calculated by the expression (3) and the actually measured first-half combustion period measured by the actual machine.
Figure 18:
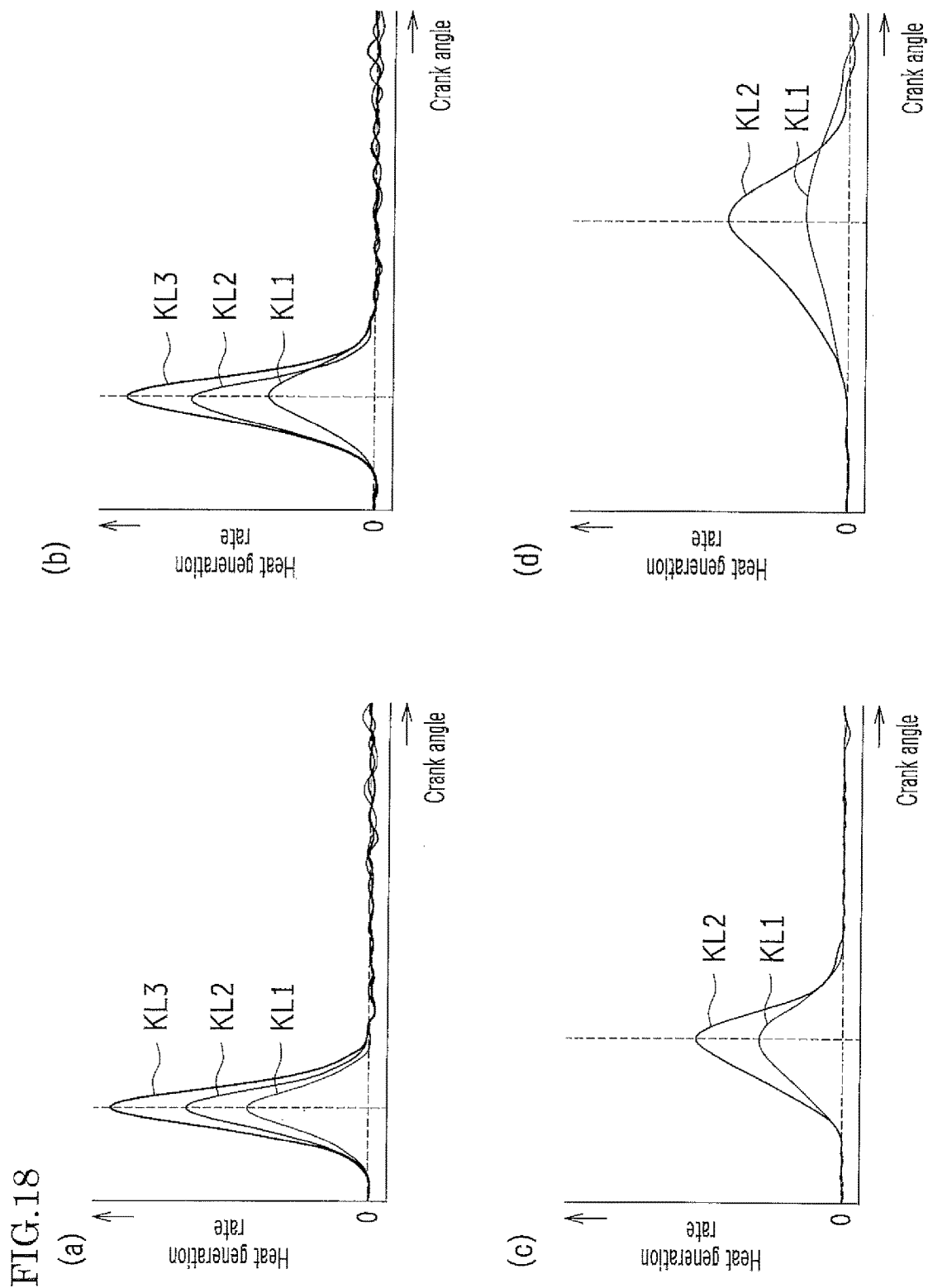
FIG. 18 are graphs indicating the heat generation rate waveforms obtained in the respective engine operation states that differ from one another only in the load rate, by adjusting each spark time SA so that the respective heat generation rate maximum times dQpeakA match with one another, the heat generation rate waveforms being indicated in a manner overlapping with one another.

FIGS. 16 and 17 are graphs indicating results obtained by verifying the relationship, in the respective engines that differ from each other, between the predicted first-half combustion period calculated by the expression (3) and the actually measured first-half combustion period measured by an actual machine. In order to obtain the predicted first-half combustion period, a prediction expression is used, which is obtained by identifying the coefficient C in the expression (3) according to the engine operation condition; In FIG. 16, the engine rotation speed Ne increases in the following order: "○"; "Δ"; "□"; "◇"; "×"; "+"; and "∇". For example, "○" represents 800 rpm, "Δ" represents 1000 rpm, "□" represents 1200 rpm, "◇" represents 1600 rpm, "×" represents 2400 rpm, "+" represents 3200 rpm and "∇" represents 3600 rpm. Also, in FIG. 17, the engine rotation speed Ne increases in the following order: "○"; "×"; "+"; "Δ"; and "□". For example, "○" represents 800 rpm, "×" represents 1200 rpm, "+" represents 2400 rpm, "Δ" represents 3600 rpm and "□" represents 4800 rpm.

As clearly shown in FIGS. 16 and 17, the predicted first-half combustion period substantially coincides with the actually measured first-half combustion period. Thus, it can be clearly seen that the first-half combustion period a is calculated with a high accuracy by the expression (3).

As described above, the first-half combustion period a can be estimated based on the in-cylinder volume $V_{@dQpeak}$ at heat generation rate maximum time and the engine rotation speed Ne, without being affected by the load rate, the air-fuel ratio, the EGR rate and the oil-water temperature. The in-cylinder volume $V_{@dQpeak}$ at heat generation rate maximum time and the engine rotation speed Ne are, as described above, the parameters correlated with the turbulence in the cylinder. In other words, it is considered that the load rate, the air-fuel ratio, the EGR rate and the oil-water temperature do not affect the first-half combustion period a because they have almost no correlation with the turbulence in the cylinder. The first-half combustion period a can be estimated based on the in-cylinder volume $V_{@dQpeak}$ at heat generation rate maximum time and the engine rotation speed Ne, which are the parameters correlated with the turbulence in the cylinder. There is no need to consider the load rate, the air-fuel ratio, the EGR rate and the oil-water temperature. Thus, it is possible to considerably reduce man-hours to determine the first-half combustion period a under various operation conditions of the engine.

As described above, the first-half combustion period is not affected by the load rate. The load rate is a parameter to control the fuel injection amount. The fuel injection amount is a control parameter that affects the in-cylinder fuel density. Thus, the first-half combustion period is estimated regardless of the in-cylinder fuel density. More specifically, as described above, the first-half combustion period is estimated based on the parameters affecting the turbulence in the cylinder such as the in-cylinder volume $V_{@dQpeak}$ at heat generation rate maximum time and the engine rotation speed Ne. On the other hand, the heat generation rate gradient is estimated based on the in-cylinder fuel density, as described later. Like this, the first-half combustion period and the heat generation rate gradient, which are to be estimated in this embodiment, are estimated respectively as the values independent from each other (i.e., values not depending from each other).

—Heat Generation Rate Gradient Estimation Part—

As described above, the heat generation rate gradient estimation part 4 estimates the gradient b/a of the heat generation rate (hereinafter referred to as "heat generation rate gradient") in the first-half combustion period.

The processing for estimating the heat generation rate gradient b/a is performed by the heat generation rate gradient estimation part 4 as described below.

The heat generation rate gradient b/a [J/CA²] is principally estimated using the following expression (4) (i.e., the expression corresponds to the heat generation rate gradient estimation model).

[Expression 4]

$$\frac{b}{a} = C_3 \times \rho_{fuel@dQpeak} \quad (4)$$

In the above expression, $\rho_{fuel@dQpeak}$ represents the fuel density at the heat generation rate maximum time dQpeakA (i.e., in-cylinder fuel amount [mol]/in-cylinder volume [L] at the heat generation rate maximum time), which is also referred to as "fuel density at heat generation rate maximum time" hereinafter. $C_3$ represents the coefficient identified by experiments and the like.

The above expression (4) holds under the condition that the engine rotation speed is fixed, the air-fuel ratio is the theoretical air-fuel ratio, the EGR rate equals zero, the warming-up operation of the engine is finished (i.e., the oil-water temperature is the predetermined value or more), and the opening/closing timing of the intake valve is fixed. Affection due to the engine rotation speed, the air-fuel ratio, the EGR rate, the oil-water temperature of the engine, and the like will be described later.

The reason why the heat generation rate gradient b/a can be calculated by the above expression (4) will be described below.

FIGS. 18(a) to 18(d) are graphs indicating respectively heat generation rate waveforms obtained in respective engine operation states that differ from one another only in the load rate, by adjusting each spark time SA so that the respective heat generation rate maximum times dQpeakA match with one another, the heat generation rate waveforms being indicated in a manner overlapping with one another. The spark time gradually changes to the delay side in the order of FIG. 18(a) to FIG. 18(d). Also, the load rate in each Figure gradually increases in the order of KL1, KL2 and KL3. For example, in FIG. 18, KL1 represents 20% load rate, KL2 represents 30% load rate, and KL3 represents 40% load rate.

As shown in FIGS. 18(a) to 18(d), the heat generation rate gradient b/a is affected by the load rate and the spark time SA. In particular, in any of FIGS. 18(a) to 18(d) that differ from one another in the spark time SA, the heat generation rate gradient b/a increases as the load rate increases. The reason why the heat generation rate gradient b/a is affected by the load rate is considered to be the change in the in-cylinder fuel density according to the load rate. That is, the greater the load rate is, the greater the fuel amount in the cylinder is, which results in the in-cylinder fuel density being greater. Thus, the combustion speed of the air-fuel mixture also increases.

Figure 19:
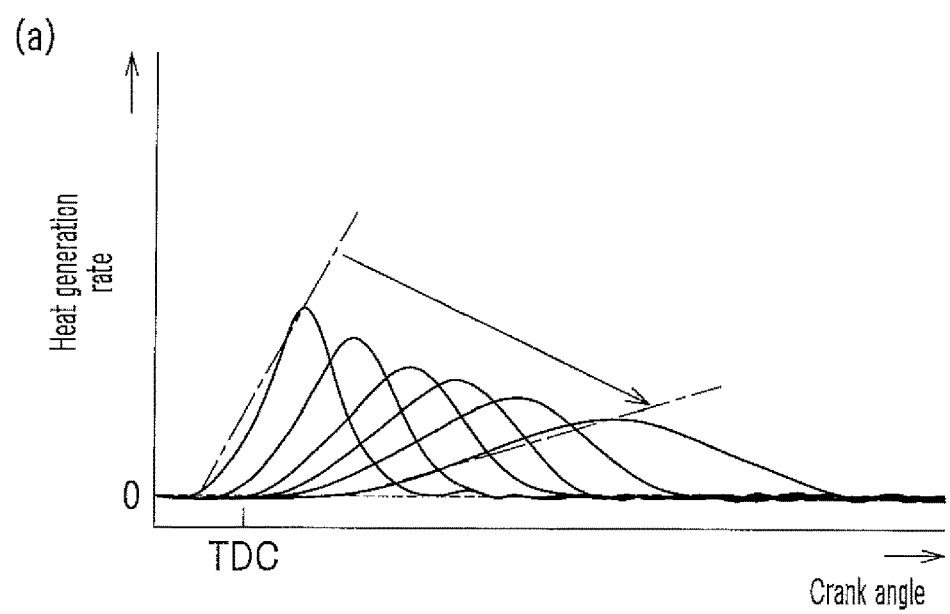
FIG. 19 are graphs indicating the heat generation rate waveforms obtained in the respective engine operation states that differ from one another only in the spark time SA, the heat generation rate waveforms being indicated in a manner overlapping with one another.
Figure 19:
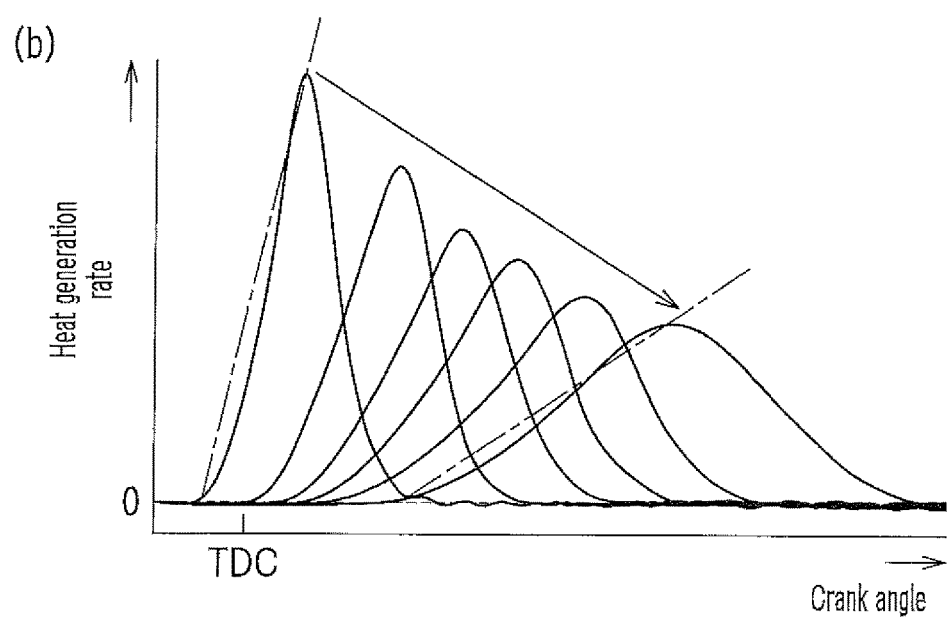

As the spark time SA is shifted to the delay side in the order of FIG. 18(a) to FIG. 18(d), the heat generation rate gradient b/a decreases. FIGS. 19(a) and 19(b) are graphs indicating, in an overlapping manner, the heat generation rate waveforms obtained in the respective engine operation states that differ from one another only in the spark time SA, in order to study the influence due to the change in the spark time SA. The respective load rates in FIGS. 19(a) and 19(b) differ from each other, however, the heat generation rate gradients b/a in both Figures tend to decrease as the spark time SA is shifted to the delay side.

Thus, the reason why the heat generation rate gradient b/a is affected by the spark time SA is considered to be the in-cylinder fuel density, similarly to the above-described affection by the load rate. That is, when the piston is in the vicinity of the compression top dead center (TDC), the change in the in-cylinder volume according to the change in the crank angle is small. As the piston moves away from the TDC in the expansion stroke (for example, from the time of about ATDC 10° CA), the in-cylinder volume increases, which results in gradual decrease in the in-cylinder fuel density.

Thus, as shown in FIGS. 19(a) and 19(b), according to the delay of the spark time SA, the heat generation rate waveform is shifted to the delay side as a whole. Furthermore, when the ignition time FA (i.e., starting point of the waveform) is after the TDC, the heat generation rate waveform gradient gradually decreases as the ignition time is delayed. As a result, the gradient of a straight line connecting the ignition time FA (starting point of the waveform) and the heat generation rate b (apex of the waveform) at the heat generation rate maximum time dQpeakA (i.e., the heat generation rate gradient b/a, which is indicated by the dashed-dotted line in the graph) also gradually decreases toward the delay side.

The influence of the delay of the spark time SA (i.e., delay of the ignition time FA) on the heat generation rate gradient b/a is clearly expressed by the relationship between the heat generation rate gradient b/a and the fuel density $\rho_{fuel@dQpeak}$ at heat generation rate maximum time. That is, as shown in FIGS. 19(a) and 19(b), the heat generation rate maximum time dQpeakA is shifted to the delay side according to the delay of the spark time SA. And as the in-cylinder volume at the heat generation rate maximum time dQpeakA (i.e., in-cylinder volume $V_{@Qpeak}$ at heat generation rate maximum time) increases, the fuel density $\rho_{fuel@dQpeak}$ at heat generation rate maximum time decreases, which leads to the decrease in the heat generation rate gradient b/a.

Figure 20:
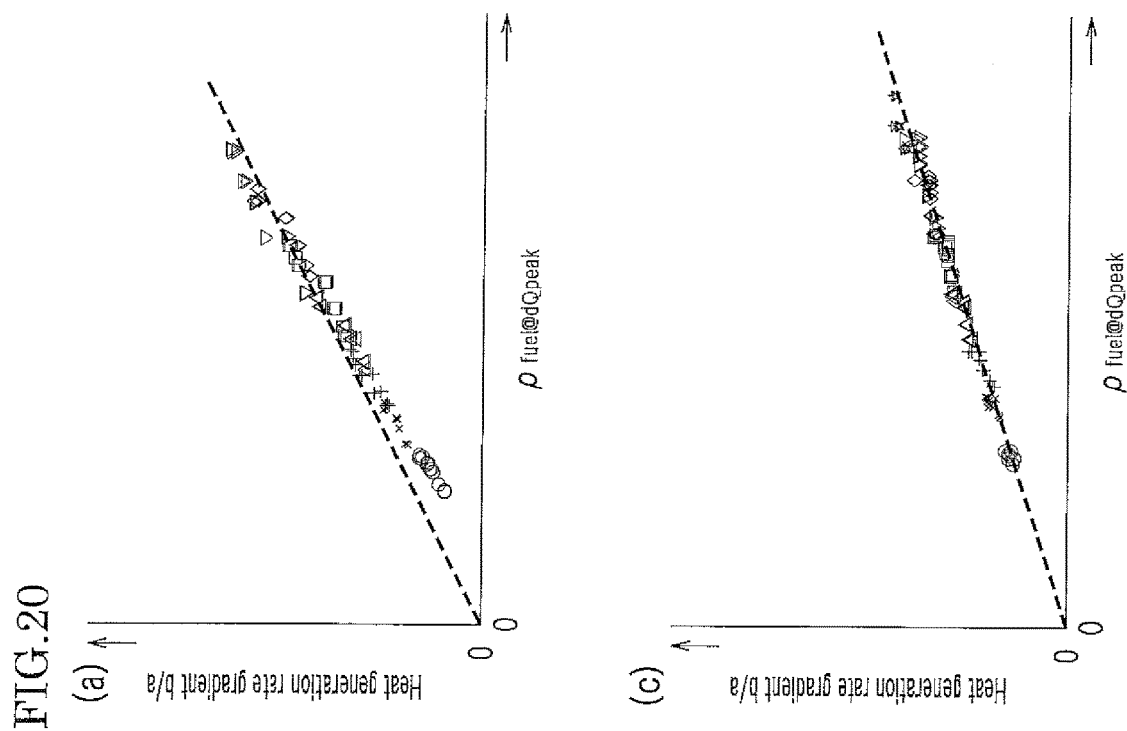
FIG. 20 are graphs indicating experimentally-obtained results of the relationship between a fuel density $\rho_{fuel@dQpeak}$ at heat generation rate maximum time and the heat generation rate gradient b/a in the respective engine rotation speeds Ne that differ from one another.

The inventor of the present invention studied the changes in the heat generation rate gradient b/a according to the changes in the fuel density $\rho_{fuel@dQpeak}$ at heat generation rate maximum time. The experiment results are indicated in the graphs in FIGS. 20(a) to 20(d). In the respective graphs, the load rate increases in the following order: "○"; "x"; "+"; "Δ"; "□"; "◊"; "∇"; and "☆". For example, in FIG. 20, "○" represents 15% load rate, "x" represents 20% load rate, "+" represents 25% load rate, "Δ" represents 30% load rate, "□" represents 35% load rate, "◊" represents 40% load rate, "∇" represents 45% load rate and "☆" represents 50% load rate.

Also, the engine rotation speed Ne increases in the order of FIG. 20(a) to FIG. 20(d). For example, the engine rotation speed Ne is 800 rpm in FIG. 20(a), 1200 rpm in FIG. 20(b), 2000 rpm in FIG. 20(c) and 3200 rpm in FIG. 20(d).

As shown in FIGS. 20(a) to 20(d), when the engine rotation speed is fixed, the relationship between the fuel density $\rho_{fuel@dQpeak}$ at heat generation rate maximum time and the heat generation rate gradient b/a can substantially be expressed by one straight line even when the respective load rates and the spark times SA differ from one another. Thus, it can be seen that the fuel density $\rho_{fuel@dQpeak}$ at heat generation rate maximum time and the heat generation rate gradient b/a have a high correlation (specifically, a substantially proportional relation) with each other. That is, the influence of the engine load rate and the spark time SA on the heat generation rate gradient b/a can be collectively expressed by one parameter, i.e., the fuel density $\rho_{fuel@dQpeak}$ at heat generation rate maximum time.

From the above-described new knowledge, the inventor of the present invention derived the above expression (4).

As described above, the fuel density $\rho_{fuel@dQpeak}$ at heat generation rate maximum time, which is the variable in the expression (4), can be obtained by dividing the in-cylinder fuel amount by the in-cylinder volume $V_{@dQpeak}$ at heat generation rate maximum time. The steps of obtaining the in-cylinder volume $V_{@dQpeak}$ at heat generation rate maximum time are described above, in the description of the first-half combustion period estimation part 3. Also, the in-cylinder fuel amount is given as the input information from the heat generation rate waveform calculation device 1.

In this way, it is possible to calculate the heat generation rate gradient b/a, which is one of the characteristic values of the heat generation rate waveform, basically as a linear function (in this embodiment, exemplarily as a proportional function) of the fuel density $\rho_{fuel@dQpeak}$ at heat generation rate maximum time. In other words, the heat generation rate gradient b/a can be estimated mainly based on the fuel density $\rho_{fuel@dQpeak}$ at heat generation rate maximum time without considering the load rate and the spark time SA. Thus, it is possible to reduce man-hours to determine the heat generation rate gradient b/a under various operation conditions of the engine.

—Heat Generation Amount Estimation Part—

As described above, the heat generation amount estimation part 5 estimates the heat generation amount (total heat generation amount $Q_{all}$) generated throughout the entire combustion period.

Hereinafter, the estimation operation performed by the heat generation amount estimation part will be described, which is to obtain the total heat generation amount $Q_{all}$.

First, the heat generation amount Q1 in the first-half combustion period a is calculated by the following expression (5).

[Expression 5]

$$Q_1 = \frac{1}{2} \times \frac{b}{a} \times a^2 \qquad (5)$$

Meanwhile, as described above, the total heat generation amount $Q_{all}$ can be expressed as the following expression: in-cylinder fuel amount×k (combustion efficiency) (i.e., the expression corresponds to the heat generation amount estimation model). When the oil-water temperature is lower, for example, during the warming-up operation, the combustion efficiency k reduces. Also, the combustion efficiency k changes due to the changes in the load rate or the engine rotation speed. Thus, in this embodiment, a map is previously set, using experimental database of the various engines, in order to determine the value of the combustion efficiency k by associating the combustion efficiency k with the oil-water temperature, the load rate and the engine rotation speed. Then, the total heat generation amount $Q_{all}$ is calculated based on the in-cylinder fuel amount, using the combustion efficiency k.

As described above with reference to FIG. 2, in order to produce the heat generation rate waveform, it is necessary to obtain the heat generation rate b at the heat generation rate maximum time dQpeakA and the second-half combustion period c. The heat generation amount Q2 in the second-half combustion period c is obtained by the following expression (6).

[Expression 6]

$$Q_2 = Q_{all} - Q_1 \qquad (6)$$

Also, the heat generation rate b at the heat generation rate maximum time dQpeakA is obtained by the following expression (7), and the second-half combustion period c is obtained by the following expression (8).

[Expression 7]

$$b = \frac{b}{a} \times a \qquad (7)$$

[Expression 8]

$$c = 2 \times \frac{Q_2}{b} \qquad (8)$$

In view of the foregoing, the following are performed in the heat generation rate waveform calculation device 1: estimation of the ignition delay period τ using the ignition delay estimation model by the ignition delay estimation part 2; estimation of the first-half combustion period a using the first-half combustion period estimation model by the first-half combustion period estimation part 3; estimation of the heat generation rate gradient b/a using the heat generation rate gradient estimation model by the heat generation rate gradient estimation part 4; estimation of the heat generation amount $Q_{all}$ using the heat generation amount estimation model by the heat generation amount estimation part 5; and calculation of the maximum heat generation rate b and the second-half combustion period c. Also, in the heat generation rate waveform calculation device 1, the triangular waveform that is approximated to the heat generation rate waveform is produced using the above calculated values, as shown in FIG. 2, thus the triangular waveform is output as the heat generation rate waveform. Using the output heat generation rate waveform, the system, control and adaptive values are reviewed when designing an engine.

As described above, in this embodiment, when the triangular waveform that is approximated to the heat generation rate waveform of the engine is produced, the first-half combustion period a, which is one of the characteristic values of the waveform, is used. Also, it was newly found that the first-half combustion period a is not affected by the operation conditions such as the engine load rate, the EGR rate, the air-fuel ratio and the oil-water temperature. That is, the first-half combustion period a is considered to be a value not affected by any of the engine load rate, the EGR rate, the air-fuel ratio and the oil-water temperature, and it is calculated based on the in-cylinder volume $V_{@dQpeak}$ at heat generation rate maximum time and the engine rotation speed Ne (more specifically, the exponential function of the engine rotation speed Ne with the value β depending on the tumble ratio as exponent). Thus, in this embodiment, the heat generation rate waveform is produced based on the first-half combustion period a, and it is not necessary to consider the above operation conditions. Accordingly, it is possible to reduce man-hours to produce the heat generation rate waveform while ensuring a sufficient accuracy compared with the conventional art in which the heat generation rate waveform is produced in consideration of (specifically, by changing) the operation conditions such as the load rate, the EGR rate, the air-fuel ratio and the oil-water temperature (i.e., the art in which a plurality of parameters such as a shape parameter is identified under the various operation conditions using the Wiebe function).

Thus, various elements for designing an engine can be effectively reviewed using the heat generation rate waveform, which leads to reduction in development cost.

Also, the heat generation rate waveform is produced based on the first-half combustion period a that is calculated based on the in-cylinder volume $V_{@dQpeak}$ at heat generation rate maximum time and the engine rotation speed Ne. Thus, the heat generation rate waveform is produced according to physical phenomena in the combustion state in the cylinder. In this respect, the heat generation rate waveform produced by the heat generation rate waveform calculation device 1 according to this embodiment can be highly reliable in comparison with the conventional method for producing the heat generation rate waveform using the Wiebe function to which various parameters such as a shape parameter are mathematically matched so as to simply match the waveform shape.

Furthermore, in this embodiment, it is not necessary to produce the entire heat generation rate waveform. As described above, the first-half combustion period a can be calculated based on the in-cylinder volume $V_{@dQpeak}$ at heat generation rate maximum time and the engine rotation speed Ne. For this reason, it is possible to simply estimate/evaluate the first-half combustion period a while ensuring a required accuracy.

Also, as described above, the first-half combustion period a and the heat generation rate gradient b/a, which are to be estimated in this embodiment, are estimated respectively as the values independent from each other (i.e., values not depending from each other). For this reason, the first-half combustion period a is estimated as a value that is not affected by an estimation error that may be included in the heat generation rate gradient b/a, while the heat generation rate gradient b/a is estimated as a value that is not affected by an estimation error that may be included in the first-half combustion period a. As a result, it is possible to ensure the accuracy in the estimated values.

Other Embodiments

The embodiment as described above is a case in which the present invention is applied to a heat generation rate waveform calculation device to produce a heat generation rate waveform of the gasoline engine for a vehicle. The present invention is not limited thereto, and it can be applied to a spark ignition engine used for other purpose than mounting on the vehicle. Also, the present invention is not limited to application to the gasoline engine, and it can be applied, for example, to a gas engine.

Also, the method for calculating the heat generation rate waveform, which is performed by the heat generation rate waveform calculation device as described in the above embodiment, is within the technical idea of the present invention.

In the embodiment as described above, the average increase rate of the heat generation rate in the period from the ignition time FA of the air-fuel mixture to the heat generation rate maximum time dQpeakA is defined as the heat generation rate gradient b/a, and the heat generation rate gradient b/a is calculated as a linear function of the fuel density $\rho_{fuel@dQpeak}$ at heat generation rate maximum time as indicated by the expression (4). However, the present invention is not limited thereto.

That is, the heat generation rate gradient may be defined to be, for example, the increase rate of the heat generation rate in the period from the ignition time to a predetermined time slightly before the heat generation rate maximum time dQpeakA, within the period in which the heat generation rate increases (heat generation rate increasing period) from the ignition time FA to the heat generation rate maximum time dQpeakA. Thus, the heat generation rate gradient may be estimated based on the fuel density in the above predetermined time.

Also, in the embodiment as described above, in order to obtain the in-cylinder volume $V_{@dQpeak}$ at heat generation rate maximum time and the first-half combustion period a, the virtual heat generation rate maximum time is set and the calculation by the expression (3) is repeatedly performed. However, the present invention is not limited thereto. The heat generation rate maximum time may be sensed by experiments using an actual machine so as to set the heat generation rate maximum time, or a desired heat generation rate maximum time may be input, as the input information, to the heat generation rate waveform calculation device 1. Thus, the in-cylinder volume $V_{@dQpeak}$ at heat generation rate maximum time and the first-half combustion period a can be obtained.

Furthermore, the method for calculating the ignition delay period τ of the air-fuel mixture in the above-described embodiment is merely one example. The present invention is not limited thereto. For example, the ignition delay period τ may be determined by experiments or simulations.

The heat generation rate waveform calculation device 1 according to the above-described embodiment is to output the triangular waveform. However, the present invention is not limited thereto. The produced triangular waveform may be subjected to predetermined filter processing so as to produce the heat generation rate waveform to output.

Also, in the above-described embodiment, the in-cylinder volume is used as the physical quantity at the heat generation rate maximum time. However, it is possible to use any other physical quantity that defines the turbulence in the cylinder (that affects the turbulence in the cylinder).

Also, in the embodiment as described above, the first-half combustion period a is calculated as a value not being affected by any of the engine load rate, the EGR rate, the air-fuel ratio and the oil-water temperature. However, the first-half combustion period a may be calculated as a value not being affected by at least one of the above operation conditions.

INDUSTRIAL APPLICABILITY

With the present invention, it is possible to reduce man-hours to produce a heat generation rate waveform of a spark-ignition internal combustion engine, and to reduce cost. Thus, it can be applied, for example, to an internal combustion engine for a vehicle.

DESCRIPTION OF REFERENCE NUMERALS

1 Heat generation rate waveform calculation device
SA Spark time
FA Ignition time of air-fuel mixture
a First-half combustion period (period from ignition time to heat generation rate maximum time)
b Heat generation rate at heat generation rate maximum time
dQpeakA Heat generation rate maximum time
$V_{@dQpeak}$ In-cylinder volume at heat generation rate maximum time
$Ne^{\beta}$ Correction coefficient based on engine rotation speed
$V_{@dQpeak}^{\alpha}$ Correction coefficient based on in-cylinder volume at heat generation rate maximum time

The invention claimed is:

1. A heat generation rate waveform calculation device of an internal combustion engine, the device being configured to calculate a heat generation rate waveform of a spark-ignition internal combustion engine,
   wherein, within a combustion period of an air-fuel mixture, a period from an ignition time to a heat generation rate maximum time where a heat generation rate is maximum is defined as a first-half combustion period that is one of characteristic values of the heat generation rate waveform,
   wherein the first-half combustion period is estimated based on a physical quantity at the heat generation rate maximum time, so that the heat generation rate waveform is calculated using the estimated first-half combustion period, and
   wherein the first-half combustion period is estimated as a value not affected by at least one of an engine load rate, an air-fuel ratio, an exhaust gas recirculation (EGR) rate and an oil-water temperature.

2. The heat generation rate waveform calculation device of an internal combustion engine according to claim 1,
   wherein the first-half combustion period is calculated based on an in-cylinder volume at the heat generation rate maximum time.

3. The heat generation rate waveform calculation device of an internal combustion engine according to claim 2,
   wherein the first-half combustion period is calculated by being multiplied by a correction coefficient based on an engine rotation speed.

4. The heat generation rate waveform calculation device of an internal combustion engine according to claim 3,
   wherein the correction coefficient based on the engine rotation speed is an exponential function of the engine rotation speed with a value depending on a tumble ratio as exponent.

5. The heat generation rate waveform calculation device of an internal combustion engine according to claim 4,
   wherein a virtual heat generation rate maximum time is set,
   wherein a virtual first-half combustion period between the ignition time obtained according to an actual spark time and the virtual heat generation rate maximum time is compared with an estimated first-half combustion period based on a physical quantity at the virtual heat generation rate maximum time so as to calculate a true first-half combustion period as the estimated first-half combustion period that coincides with the virtual first-half combustion period, and
   wherein the heat generation rate waveform is calculated using the true first-half combustion period.

6. The heat generation rate waveform calculation device of an internal combustion engine according to claim 5,
   wherein the heat generation rate waveform is approximated by a triangular waveform with a crank angle period from the ignition of the air-fuel mixture to combustion completion as a base and the heat generation rate at the heat generation rate maximum time as an apex, and wherein, in the triangular waveform, the base of the triangle, which represents the heat generation rate from the ignition time to the heat generation rate maximum time, is defined as the first-half combustion period.

7. The heat generation rate waveform calculation device of an internal combustion engine according to claim 4, wherein the heat generation rate waveform is approximated by a triangular waveform with a crank angle period from the ignition of the air-fuel mixture to combustion completion as a base and the heat generation rate at the heat generation rate maximum time as an apex, and wherein, in the triangular waveform, the base of the triangle, which represents the heat generation rate from the ignition time to the heat generation rate maximum time, is defined as the first-half combustion period.

8. The heat generation rate waveform calculation device of an internal combustion engine according to claim 3, wherein a virtual heat generation rate maximum time is set, wherein a virtual first-half combustion period between the ignition time obtained according to an actual spark time and the virtual heat generation rate maximum time is compared with an estimated first-half combustion period based on a physical quantity at the virtual heat generation rate maximum time so as to calculate a true first-half combustion period as the estimated first-half combustion period that coincides with the virtual first-half combustion period, and wherein the heat generation rate waveform is calculated using the true first-half combustion period.

9. The heat generation rate waveform calculation device of an internal combustion engine according to claim 8, wherein the heat generation rate waveform is approximated by a triangular waveform with a crank angle period from the ignition of the air-fuel mixture to combustion completion as a base and the heat generation rate at the heat generation rate maximum time as an apex, and wherein, in the triangular waveform, the base of the triangle, which represents the heat generation rate from the ignition time to the heat generation rate maximum time, is defined as the first-half combustion period.

10. The heat generation rate waveform calculation device of an internal combustion engine according to claim 3, wherein the heat generation rate waveform is approximated by a triangular waveform with a crank angle period from the ignition of the air-fuel mixture to combustion completion as a base and the heat generation rate at the heat generation rate maximum time as an apex, and wherein, in the triangular waveform, the base of the triangle, which represents the heat generation rate from the ignition time to the heat generation rate maximum time, is defined as the first-half combustion period.

11. The heat generation rate waveform calculation device of an internal combustion engine according to claim 2, wherein a virtual heat generation rate maximum time is set, wherein a virtual first-half combustion period between the ignition time obtained according to an actual spark time and the virtual heat generation rate maximum time is compared with an estimated first-half combustion period based on a physical quantity at the virtual heat generation rate maximum time so as to calculate a true first-half combustion period as the estimated first-half combustion period that coincides with the virtual first-half combustion period, and wherein the heat generation rate waveform is calculated using the true first-half combustion period.

12. The heat generation rate waveform calculation device of an internal combustion engine according to claim 11, wherein the heat generation rate waveform is approximated by a triangular waveform with a crank angle period from the ignition of the air-fuel mixture to combustion completion as a base and the heat generation rate at the heat generation rate maximum time as an apex, and wherein, in the triangular waveform, the base of the triangle, which represents the heat generation rate from the ignition time to the heat generation rate maximum time, is defined as the first-half combustion period.

13. The heat generation rate waveform calculation device of an internal combustion engine according to claim 2, wherein the heat generation rate waveform is approximated by a triangular waveform with a crank angle period from the ignition of the air-fuel mixture to combustion completion as a base and the heat generation rate at the heat generation rate maximum time as an apex, and wherein, in the triangular waveform, the base of the triangle, which represents the heat generation rate from the ignition time to the heat generation rate maximum time, is defined as the first-half combustion period.

14. The heat generation rate waveform calculation device of an internal combustion engine according to claim 1, wherein a virtual heat generation rate maximum time is set, wherein a virtual first-half combustion period between the ignition time obtained according to an actual spark time and the virtual heat generation rate maximum time is compared with an estimated first-half combustion period based on a physical quantity at the virtual heat generation rate maximum time so as to calculate a true first-half combustion period as the estimated first-half combustion period that coincides with the virtual first-half combustion period, and wherein the heat generation rate waveform is calculated using the true first-half combustion period.

15. The heat generation rate waveform calculation device of an internal combustion engine according to claim 14, wherein the heat generation rate waveform is approximated by a triangular waveform with a crank angle period from the ignition of the air-fuel mixture to combustion completion as a base and the heat generation rate at the heat generation rate maximum time as an apex, and wherein, in the triangular waveform, the base of the triangle, which represents the heat generation rate from the ignition time to the heat generation rate maximum time, is defined as the first-half combustion period.

16. The heat generation rate waveform calculation device of an internal combustion engine according to claim 1, wherein the heat generation rate waveform is approximated by a triangular waveform with a crank angle period from the ignition of the air-fuel mixture to combustion completion as a base and the heat generation rate at the heat generation rate maximum time as an apex, and wherein, in the triangular waveform, the base of the triangle, which represents the heat generation rate from the ignition time to the heat generation rate maximum time, is defined as the first-half combustion period.

17. A method for calculating a heat generation rate waveform of a spark-ignition internal combustion engine, comprising the steps of:
defining, within a combustion period of an air-fuel mixture, a period from an ignition time to a heat generation rate maximum time where a heat generation rate is maximum as a first-half combustion period that is one of characteristic values of the heat generation rate waveform;
estimating the first-half combustion period based on a physical quantity at the heat generation rate maximum time;
calculating the heat generation rate waveform using the estimated first-half combustion period, and
estimating the first-half combustion period as a value not affected by at least one of an engine load rate, an air-fuel ratio, an exhaust gas recirculation (EGR) rate and an oil-water temperature.

* * * * *